United States Patent [19]

Grupp et al.

[11] Patent Number: 5,110,813
[45] Date of Patent: May 5, 1992

[54] REDUCTION OF VOLUNTARY ALCOHOL CONSUMPTION BY TREATMENT WITH ANGIOTENSIN CONVERTING ENZYME INHIBITORS

[75] Inventors: Larry A. Grupp, Downsview; Edward Perlanski, Bear River, both of Canada; Robert B. Stewart, Indianapolis, Ind.

[73] Assignee: Alcoholism and Drug Addiction Research Foundation, Ontario, Canada

[21] Appl. No.: 414,952

[22] Filed: Sep. 29, 1989

Related U.S. Application Data

[63] Continuation-in-part of Ser. No. 96,951, Sep. 15, 1987.

[51] Int. Cl.⁵ .................. A61K 31/55; A61K 31/40
[52] U.S. Cl. .................. 514/212; 514/221; 514/414; 514/422; 514/423; 514/811
[58] Field of Search .............. 514/414, 422, 423, 212, 514/221, 811

[56] References Cited

U.S. PATENT DOCUMENTS

| | | | |
|---|---|---|---|
| 4,470,988 | 9/1984 | Watthey | 514/183 |
| 4,474,778 | 10/1984 | Gordan et al. | 514/183 |
| 4,656,188 | 4/1987 | Veber et al. | 514/423 |
| 4,785,089 | 11/1988 | Blaser et al. | 540/523 |
| 4,816,466 | 3/1989 | Sugihara et al. | 514/319 |
| 4,871,842 | 10/1989 | Sugihara et al. | 540/523 |

OTHER PUBLICATIONS

Grupp LA, Stewart RB, Perlanski E: Salt Restriction and the Voluntary Intake of Ethanol in Rats, Physiol. Psychol. 12:242-246, 1984.

Grupp, LA, Stewart RB, Perlanski E: Dietary Salt and Doca Salt Treatments Modify Ethanol Self-Selection in Rats, Behav Neural Biol. 40:239-250, 1984.

Grupp, LA, Stewart, RB, Perlanski, E: Diet and Diuretics in the Reduction of Voluntary Alcohol Drinking in Rats. Alcohol and Alcoholism 21: 75-79, 1986.

Grupp, LA, Perlanski, E, Wanless IR, Stewart RB: Voluntary Alcohol Intake in the Hypertensive Prone Dahl Rat. Pharmacol Biochem Behav 24:1167-1174, 1986.

Grupp LA, Perlanski E, Leenen FHH, Stewart RB: Renal Artery Stenosis: An Example of How the Periphery Can Modulate Voluntary Alcohol Drinking. Life Sci 40:563:570, 1987.

LeBlanc AE: Microdetermination of Alcohol in Blood by Gas-Liquid Chromatography, Can J. Physiol Pharmacol 46:665-667, 1968.

Linseman M: Alcohol Consumption in Free-Feeding Rats-Procedural Genetic and Pharmacokinetic Factors. Psychopharmacology 92:254-261, 1987.

Ashley, MJ, Rankin JG: Alcohol Consumption and Hypertension: The Evidence from Hazardous Drinking Alcohol Populations. Austr. New Zealand J. Med. 9:201-206, 1979.

Klatsky AL, Freedman GD, Seigelaub AB, Gerard MJ: Alcohol Consumption and Blood Pressure, New Engl. J. Med. 296: 1194-1200, 1977.

Goldblatt H, Lynch J, Hanzal RF, Summerville WW: Studies on Experimental Hypertension. I. The Production of Persistent Elevation of the Systolic Blood Pressure by Means of Renal Ischemia. J Exp Med 59:347-360, 1934.

Leenen FHH, Myers MG: Pressor Mechanisms in Renovascular Hypertensive Rats, in de Jong W (ed): Handbook of Hypertension: Experimental and Genetic Models of Hypertension, vol. 4, Amsterdam, Elsevier, 1971, pp. 24-53.

(List continued on next page.)

Primary Examiner—Glennon H. Hollrah
Assistant Examiner—Gary E. Hollinden
Attorney, Agent, or Firm—Weingarten, Schurgin, Gagnebin & Hayes

[57] ABSTRACT

A method of use of an angiotensin converting enzyme inhibitor is provided which comprises administration of the inhibitor to warm-blooded animals so as to reduce their voluntary alcohol consumption. The method further includes combining the use of opiate receptor antagonist to further reduce alcohol consumption.

11 Claims, 14 Drawing Sheets

OTHER PUBLICATIONS

Schiffrin EL, Gutkowska J, Genest J: Mechanism of Captopril Induced Renin Release. Proc Soc Exp Biol Med 167:327-332, 1981.

Schiffrin EL, Gutkowska J, Thibault G, Genest J: Effect of Enalapril (MK-421), An Orally Active Angiotensin I Converting Enzyme Inhibitor, On Blood Pressure, Active and Inactive Plasma Renin, Urinary Prostaglandin $E_2$ and Kallikrein Excretion in Conscious Rats. Can J Physiol Pharmacol 62:116-123, 1984.

Gill K, France C, Amit Z: Voluntary Ethanol Consumption in Rats: An Examination of Blood/Brain Ethanol Levels and Behavior. Alcoholism: Clin Exp Res 10:457-462, 1986.

Meshcheryakov, AF et al Chem. Abstracts 104:83598r (1986) In: Fiziol. Zh. Sssrim. I. M. Sechnova 71(12):1546-52 (1985).

REDUCTION OF VOLUNTARY ALCOHOL CONSUMPTION BY TREATMENT WITH ANGIOTENSIN CONVERTING ENZYME INHIBITORS

This application is a continuation-in-part of Ser. No. 07/096,951 filed Sep. 15, 1987; still pending.

FIELD OF THE INVENTION

The present invention relates to a new method of treatment to reduce voluntary alcohol intake in warm-blooded animals

BACKGROUND OF THE INVENTION

Although alcohol abuse is a serious problem in our society, effective treatments for reducing voluntary alcohol consumption are lacking.

One commonly used treatment is the administration of an alcohol-sensitizing drug, of which disulfiram (Antabuse: trade mark of Ayerst) is probably the best known. Such drugs do not reduce alcohol intake by interference with the biological mechanisms involved in alcohol intake, but rather induce an aversive reaction to consumed alcohol in the subject, so as to deter further drinking. Such treatment is unpleasant for the subject, should alcohol be consumed; patient compliance is poor, and evidence of the treatment's effectiveness is weak.

Another approach has been the use of agents which alter neurochemical activity, for example the administration of antidepressants such as lithium.

Indications that brain serotonin levels may be low in alcoholics have led to treatment with drugs which are serotonin uptake inhibitors, such as zimelidine and citalopram.

None of these treatments has proved particularly effective.

Recent studies by the inventors have shown that various manipulations which are known to affect the renin-angiotensin system, such as restriction of salt intake and administration of diuretics, also modulate voluntary alcohol consumption in rats.

One class of agents which affect the renin-angiotensin system is the angiotensin converting enzyme (ACE) inhibitors which prevent conversion of angiotensin I to angiotensin II. These agents are known to be useful in the treatment of hypertension and such use has shown them to be safe and without significant side-effects.

SUMMARY OF THE INVENTION

The present invention provides a method of treating warmblooded animals so as to reduce their voluntary alcohol consumption which comprises administering an angiotensin converting (ACE) enzyme inhibitor to the animals.

In accordance with the present invention, administration of angiotensin converting enzyme inhibitors such as captopril or enalapril to rats reduced their voluntary alcohol consumption specifically, across a wide spectrum of conditions and without deleterious side effects.

While the effectiveness of the ACE inhibitors has been demonstrated in the case of hypertensive animal subjects, it has been found that some ACE inhibitors are substantially ineffective in animals with suppressed renin angiotensin (RAS) systems.

Experiment demonstrated that Abutapril, a new ACE inhibitor, significantly reduces alcohol intake and that this effect may not be blocked by either an agiotensin II or an opiate receptor antagonist, suggesting that neither the peripheral renin-angiotensin system (RAS) nor the endogenous enkephalins are involved in the ability of ACE inhibition to attenuate alcohol intake Experiments further showed that ACE inhibition effectively reduces alcohol drinking faster in animals with elevated RAS activity and not at all in animals with suppressed RAS activity, indicating that initial levels of RAS activity may determine the speed and ability of certain ACE inhibitors to attenuate alcohol intake, ACE inhibitors may reduce alcohol intake by elevating a nonapeptide fragment or by elevating central angiotensin II levels. The assessment of this class of drugs to reduce alcohol intake in humans should include a monitoring of the initial level of activity in the RAS system since this may be a predictor of the effectiveness of treatment with the ACE inhibitors.

DESCRIPTION OF DRAWINGS

The method of treatment in accordance with the present invention will now be described by way of example and with reference to the drawings in which.

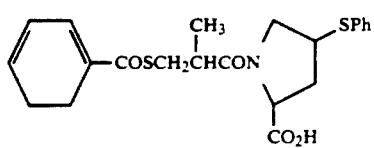

ZOFENOPRIL
SQ 26,991

-continued

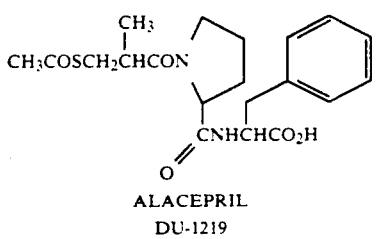

ALACEPRIL
DU-1219

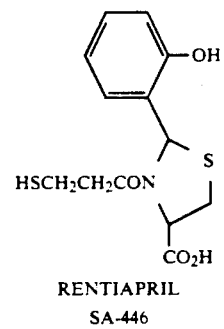

RENTIAPRIL
SA-446

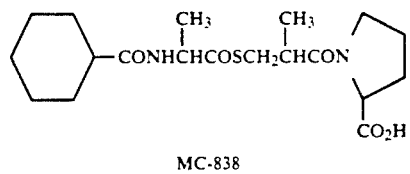

MC-838

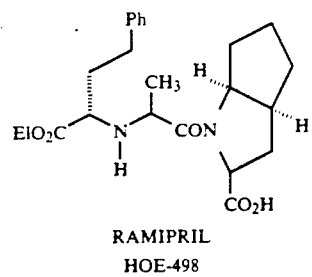

RAMIPRIL
HOE-498

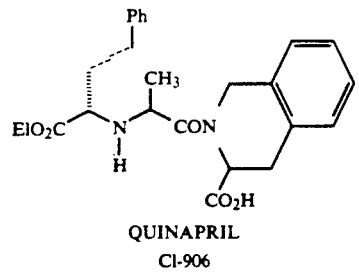

QUINAPRIL
CI-906

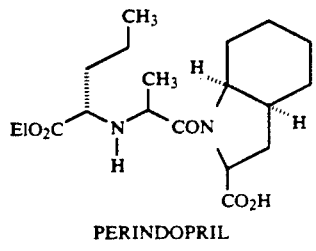

PERINDOPRIL
S-94903

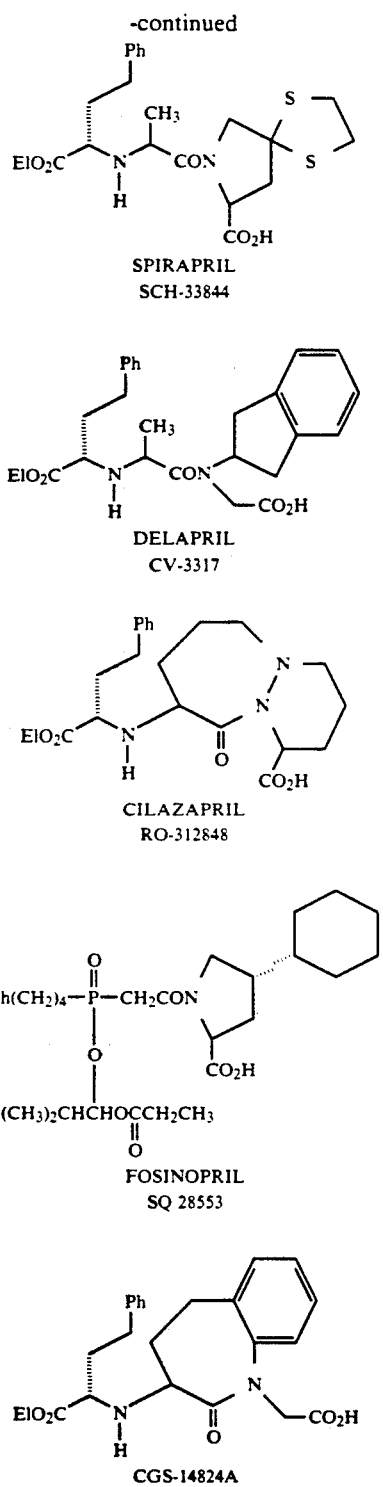

SPIRAPRIL
SCH-33844

DELAPRIL
CV-3317

CILAZAPRIL
RO-312848

FOSINOPRIL
SQ 28553

CGS-14824A

LYCINAPRIL

ABUTAPRIL (CGS-16617)

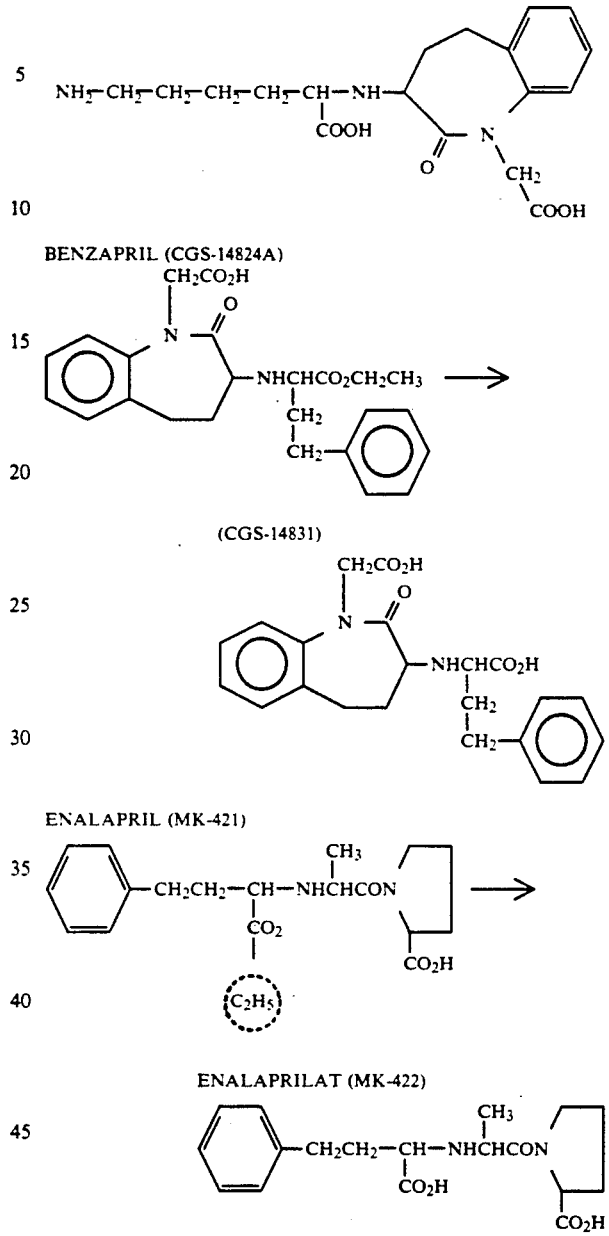

BENZAPRIL (CGS-14824A)

(CGS-14831)

ENALAPRIL (MK-421)

ENALAPRILAT (MK-422)

Figure 15A:
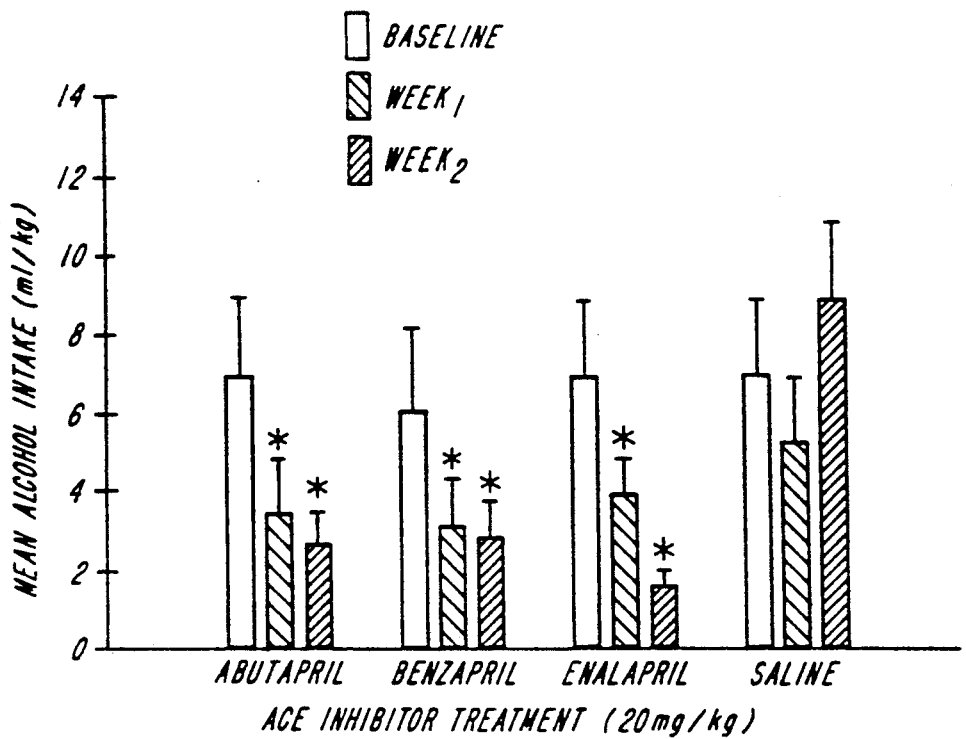
FIG. 15A is a bar diagram showing mean alcohol intake (ml/kg) in Two Kidney, (T-K), One-Clip (O-C) hypertensive animals which received either saline of three different ACE inhibitors across the Baseline phase and two week Treatment phase.
Figure 15B:
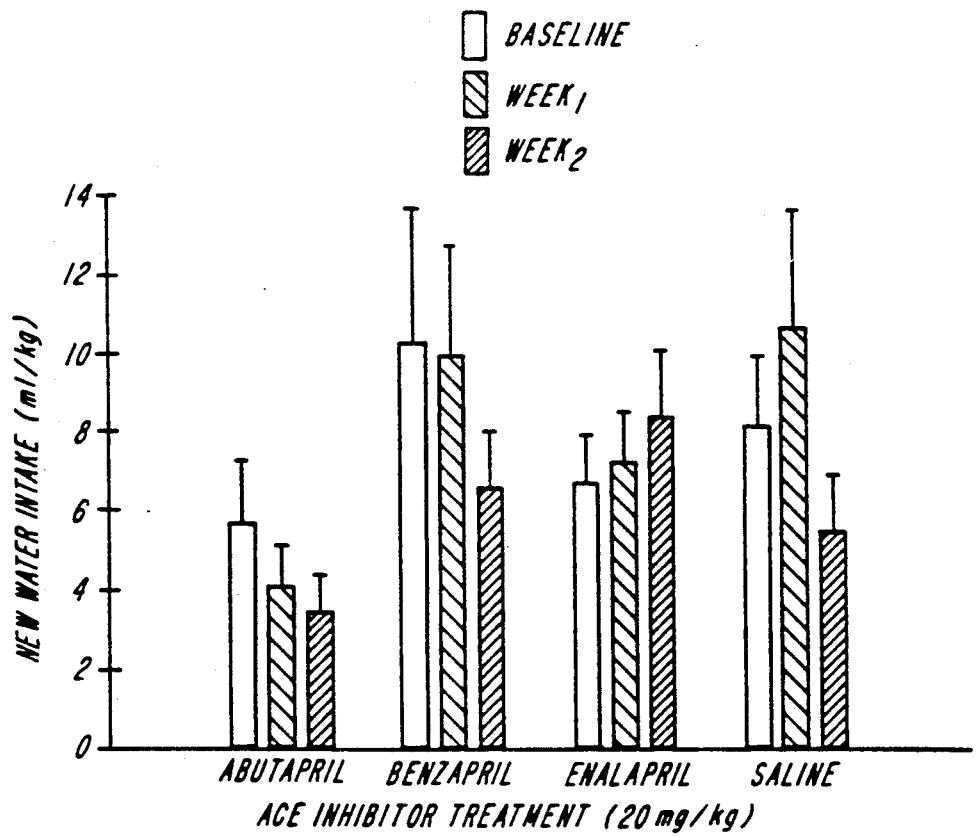
FIG. 15B is a bar diagram showing mean Water intake (ml/kg) in T-K,O-C saline group and ACE inhibitor treated groups across the Baseline phase and two week Treatment phase in Experiment six. Vertical lines represent the standard error of the mean.
Figure 15C:
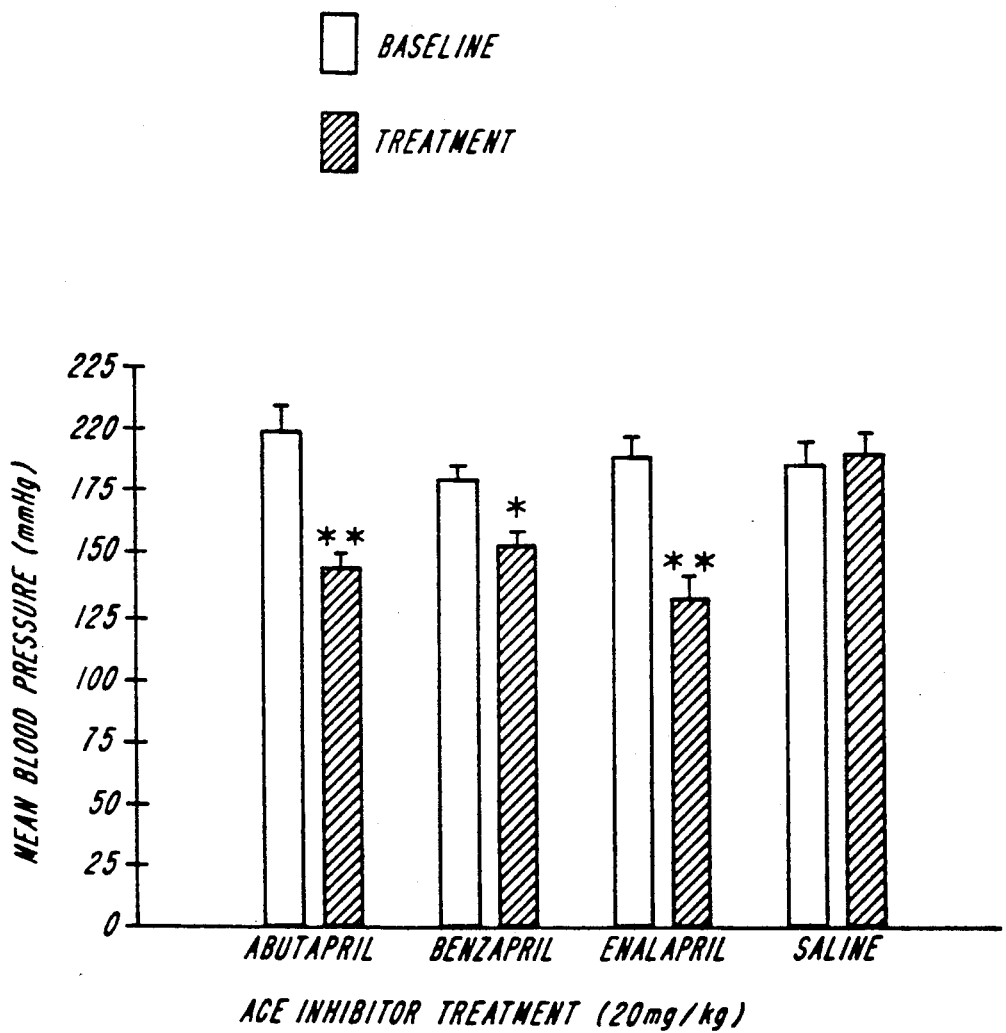

FIG. 15C is a bar diagram showing mean blood pressure in T-K,O-C hypertensive rates before (Baseline), and after ACE inhibitor treatment.

Angiotension Converting Enzyme (ACE) Inhibitors

The following group of ACE inhibitors are listed for use in carrying out the invention.

EXAMPLE 1

Treatment of rats with captopril (Capoten) under conditions of free access to alcohol.

Subjects: Thirty-six naive male Wistar rats (Charles River, Montreal) were used, weighing between 254 and 327 g at the beginning of the study. The animals were individually housed in cages equipped with a glass feeder cup containing Purina Rat Chow and two graduated drinking tubes spaced 15 cm apart. A reversed 12 hr/12 hr light/dark cycle was in effect throughout.

Procedure: All animals were allowed free access to the two drinking tubes, one containing 4% alcohol (ethanol, w/v) made up in tap water and the other containing only tap water. The positions of the two tubes were alternated daily and fluid consumption was measured over consecutive 24 hr. periods.

The study was divided into two phases. During Phase 1 (14 days) all rats were injected with 0.9% saline intraperitoneally (i.p) twice per day, once in the morning and again in the early afternoon. At the end of this phase, the rats were divided equally into four groups for alcohol consumption. In phase 2 (19 days) three of the four groups received doses of 25, 50 or 100 mg/kg captopril, respectively, in each of the two daily injections. The fourth group continued to receive 0.9% saline. Captopril was prepared in 0.9% saline and injected in concentrations adjusted so that the various doses were all administered in a volume of 1 ml/100 g body weight.

At the end of the study, five rats from each group were injected i.p. with a dose of 2.5 g/kg alcohol [12.5% (w/v)]. Blood samples were taken from the cut tip of the tail at intervals of 15 min. during the first hour after the injection and thereafter at hourly intervals for the next four hours These blood samples were prepared and analyzed by gas-liquid chromatography according to the method of LeBlanc, (Canadian Journal of Physiology and Pharmacology, (1968), v. 46, p. 665) and were used to examine the effect of captopril treatment on the pharmacokinetics of alcohol.

Figure 1A:
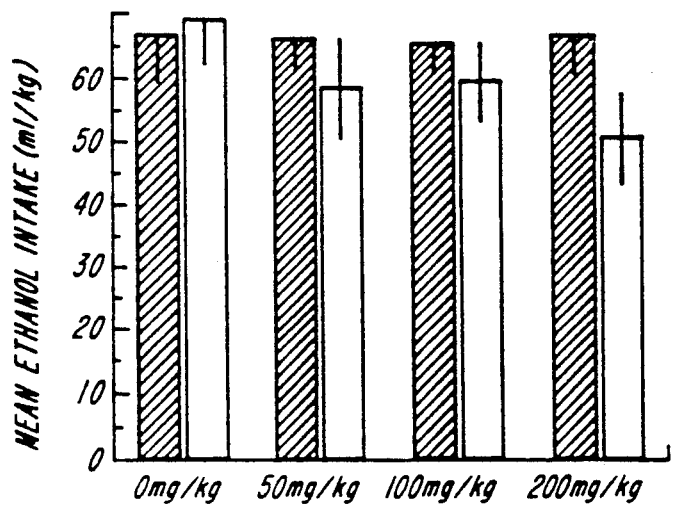
FIG. 1A and B are bar diagram showing, in FIG. 1A, mean 24-hr. alcohol intake and in FIG. 1B, mean 24-hr. water intake of rats over two time periods, phase 1 solid bars;-ACE-inhibitor absent; and phase 2 solid open bars;-ACE inhibitor present
Figure 1B:
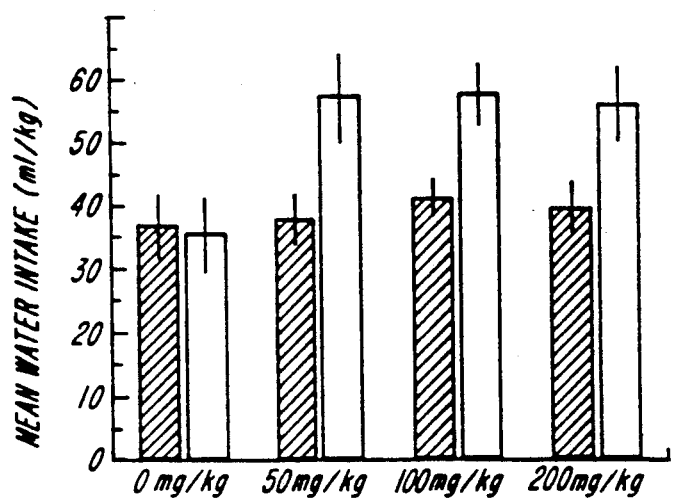

FIG. 1 shows the mean 24-hr alcohol intake (panel a) and water intake (panel b) over phase 1 (solid bars) and phase 2 (open bars) for the group treated with saline only (0 mg/kg) and the three groups treated With captopril at the indicated doses A two way analysis of variance of the 24-hr. alcohol intake data in the three captopril-treated groups of Example 1 (FIG. 1a) revealed a non-significant effect of Dose [$F(2,24)=0.10$, n.s.], a significant effect of Phase [$F(1,24)$ 11.60, $p<0.002$] and a non-significant Dose x Phase interaction [$F(2,34)=1.03$, n.s.]. Analysis showed that captopril treatment in phase 2 significantly decreased alcohol intake compared to control drinking in phase 1 ($T_{26}=3.40$, p 0.01). This decrease, however, was not dose dependent. The saline group (0 mg/kg, FIG. 1a) as expected did not alter its alcohol intake across the two phases ($T_8=0.54$, n.s.). These results indicate that captopril treatment can attenuate voluntary alcohol intake.

A two-way analysis of variance of the 24 hr. water intake data in the three captopril-treated groups of Example 1 (FIG. 1b) showed a non-significant effect of Dose [$F(2,24)=0.05$, n.s.], a significant effect of Phase [$F(1,24)=25.68$, $p<0.02$] and a non-significant Dose x Phase interaction [$F(2,24)=0.10$, n.s.]. Analysis showed that captopril treatment significantly increased water intake in phase 2 compared to control drinking in phase 1 ($T_{26}=-5.25$, $p<0.01$). Again, this effect was not dose dependent. Water intake in the saline group (FIG. 1b) did not change ($T_8=0.45$, n.s). These results indicate that captopril treatment can also increase water intake.

Figure 2:
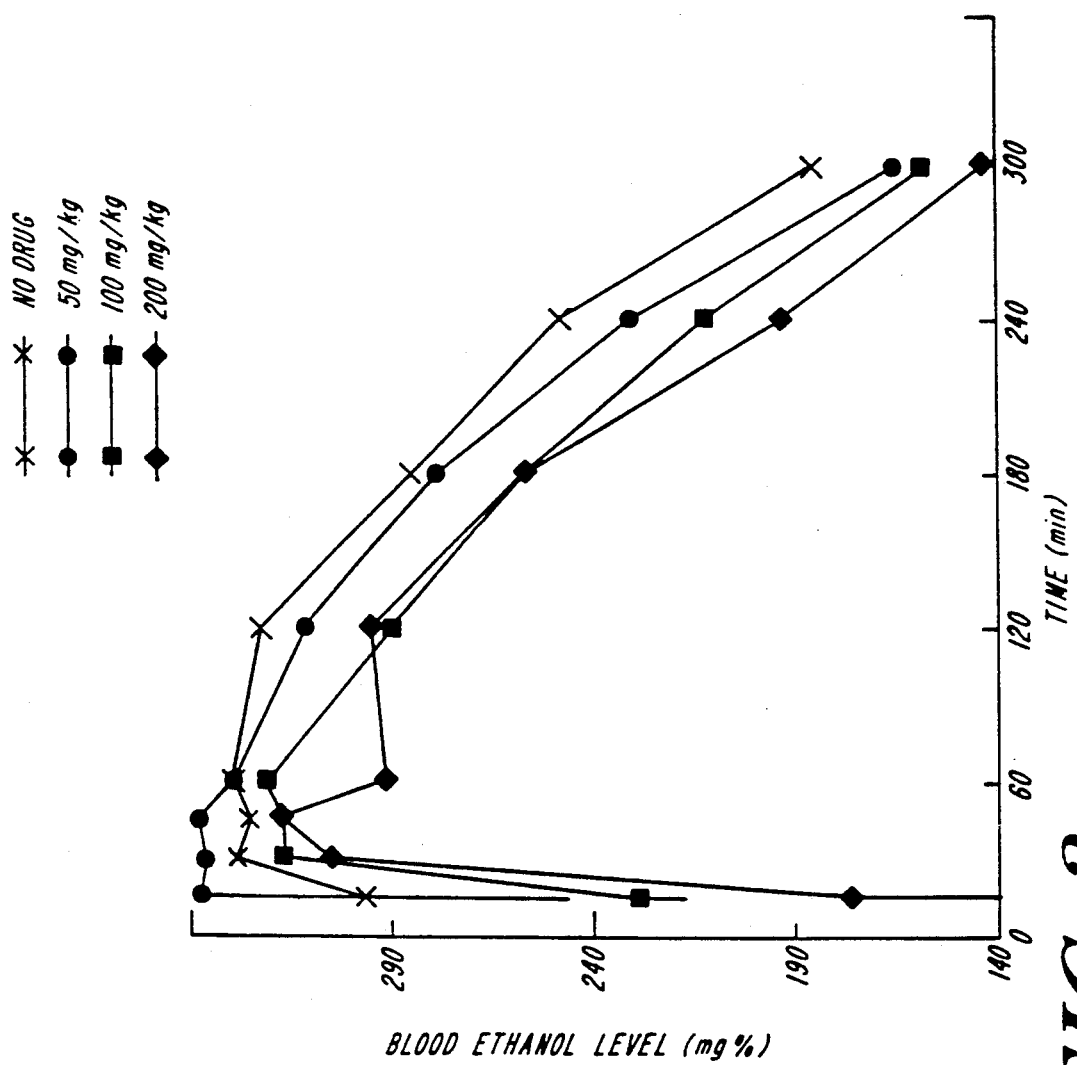
FIG. 2 is a graph showing blood alcohol levels (mg %) of the four treatment groups measured at various times (min) after an initial dose of 2.5 g/kg alcohol injected i.p. at time zero. Vertical lines represent the standard error of the mean, FIG. 3A and B are bar diagrams showing mean 24-hr. alcohol intake (ml/kg) before (baseline) and during captopril treatment in normotensive (3A) and hypertensive (3B) rats. Vertical lines represent standard error of the mean.

FIG. 2 shows the mean blood alcohol levels for the four groups of rats in Example 1 at the eight sampling times The last four points on the descending portion of the curves were used to calculate the slopes. These slopes of the linear portion of the curves represent the rate of alcohol metabolism. A one way analysis of variance of the rates of alcohol metabolism showed a non-significant effect of Group [$F(3,16)=0.93$, n.s.] indicating that captopril treatment did not change the rate of alcohol metabolism. Extension of the linear portions of the curves back to the ordinate allowed for the determination of concentrations at time zero in each rat in the respective groups. These values were used to calculate the volumes of distribution. A one-way analysis of variance of the volume of distribution data showed a non-significant effect of Group [$F(3,16)=2.25$, n.s.] indicating that captopril treatment also did not change the volume of distribution. A two-way analysis of variance of the blood alcohol levels measured at the first three time intervals following the alcohol injections (i.e. 15, 30 and 45 min) showed a non-significant effect of Group [$F(3,16)=2.62$, n.s.], a significant effect of Interval [$F(2,32)=15.06$, $p<0.01$] and a significant Group x Interval interaction [$F(6,32)=3.48$, $p<0.01$]. The significant Group x Interval interaction indicates that the two higher doses of captopril slowed the absorption of alcohol but only during the first 15 min. following the injection.

Example 1 demonstrated that captopril can reduce the voluntary intake of alcohol and that this effect is not due to a change in the distribution or metabolism of alcohol Since alcohol was self-administered orally by the animals but given by injection to study the pharmacokinetics, the slower alcohol absorption in the groups treated with captopril may not be an accurate reflection of absorption from the stomach after oral intake. Furthermore, the difference in absorption between the captopril and vehicle treated groups could account for the difference in intake only if alcohol intake varied directly with rate of absorption. However, it has been suggested that alcohol intake varies inversely, not directly with rate of absorption.

Since water intake was not likewise depressed, but in fact enhanced by captopril, the attenuation appears to be specific to alcohol rather than a generalized effect on all available fluids. Furthermore, since water intake increased following captopril treatment, it appears that the animals were healthy and attempting to maintain a normal fluid balance. The vehicle injected group did not show changes in either alcohol or water intake, indicating that injections per se did not alter fluid intake and also that the pattern of alcohol intake did not change over the course of the study.

EXAMPLE 2

Since there is a correlation between alcohol consumption and hypertension in humans, it was of interest to examine the effect of captopril on alcohol intake in hypertensive animals. Accordingly, the effect of captopril on alcohol intake was examined in animals rendered hypertensive by the Two-Kidney, One-Clip (T-K,O-C) model of hypertension described by Goldblatt et al., (1934), Journal of Experimental Medicine, v. 59, p. 347. In this model, one renal artery is constricted (renal artery stenosis) while the contralateral kidney is untouched. Reninangiotensin activity becomes elevated two to three weeks following this procedure and remains elevated thereafter for several months.

Subjects: Twenty-seven naive male Wistar rats (140-160 g) were used. All feeding and housing conditions were the same as in Example 1.

Procedure: The animals were anaesthetized with a mixture of halothane and oxygen and either had a 0.2 mm solid silver clip applied to the left renal artery (hypertensive group, n=11) or underwent a sham procedure including all surgery but no clip (normotensive group, n=16). The right kidney was left untouched. Three weeks following the operation, when both blood pressure (BP) and plasma renin activity (PRA) are elevated in the clipped animals, systolic BP was measured in both groups.

Animals were then offered free access to both alcohol (4%, w/v) and water. The positions of the two tubes were alternated daily and consumption was measured over consecutive 24 hr. periods. After the first 12 days, each animal received one 2.5 g/kg intraperitoneal (i.p.) injection of alcohol in order to establish an alcohol disappearance curve. For the next eleven days, animals were again offered free access to alcohol and water and then both groups received captopril injections i.p. twice daily in a dose of 50 mg/kg/injection for 11 days and then in a dose of 100 mg/kg/injection for a further 11 days Blood pressure was again measured at the end of the study.

Figure 3A:
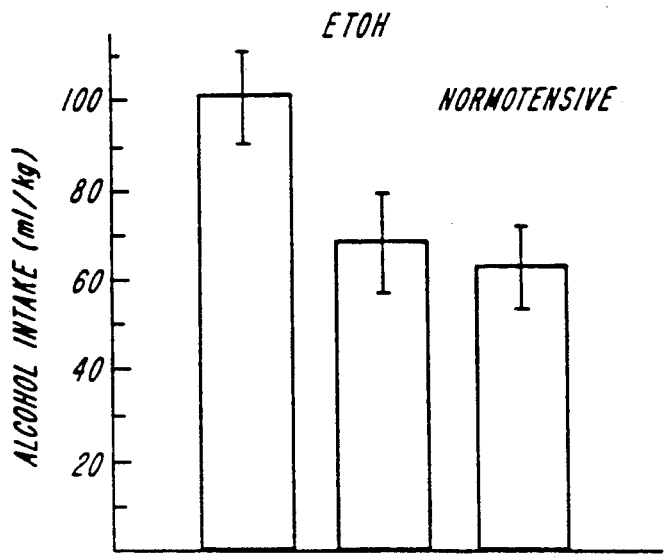
Figure 3B:
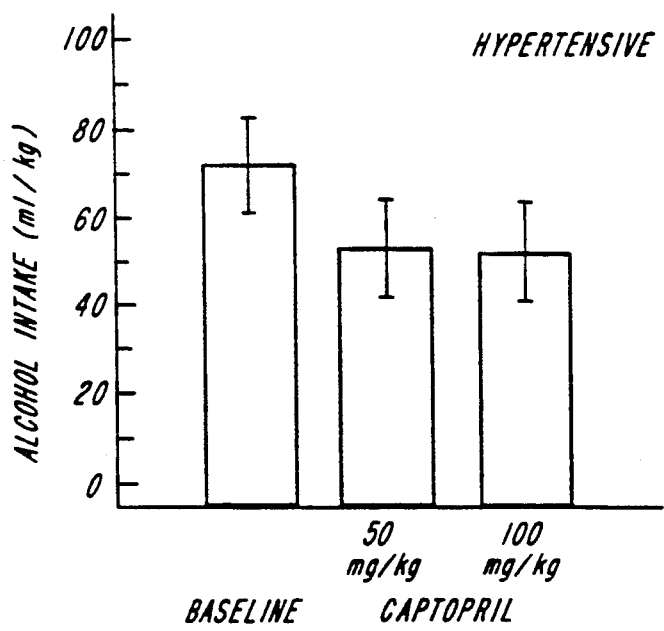

FIG. 3 illustrates the effect of the two doses of captopril on alcohol drinking in the normotensive and hypertensive groups of Example 2. FIG. 3A shows that captopril significantly reduced voluntary alcohol intake in the normotensive group [$F(2,30)=25.3$, $p <0.001$] and both the 50 mg/kg ($T_{15}=4.4$, $p <0.01$) and the 100 mg/kg doses ($T_{15}=7.2$, $p <0.01$) were effective. FIG. 3B shows that captopril also attenuated alcohol intake in the hypertensive group, although the reduction did not reach statistical significance [$F(2,20)=1.8$, n.s.].

Figure 4A:
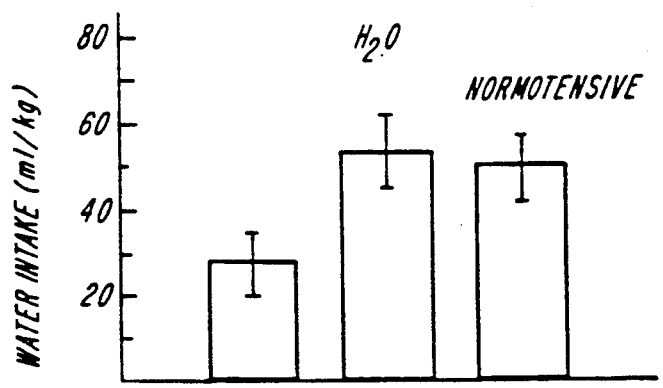
FIG. 4 is a bar diagram showing mean 24-hr. water intake (ml/kg) before (baseline) and during captopril treatment in normotensive (A) and hypertensive (B) rats. Vertical lines represent standard error of the mean.
Figure 4B:
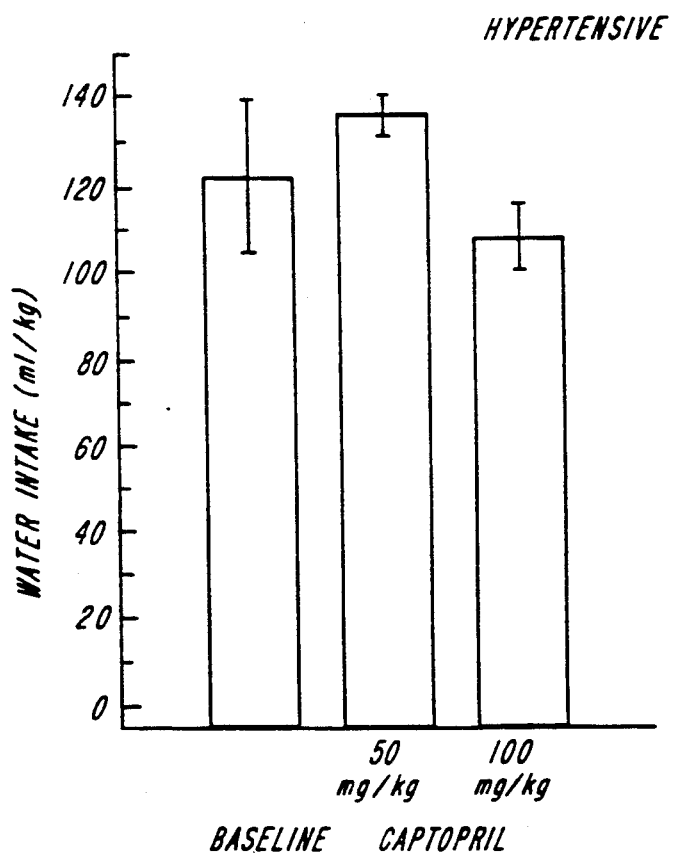

FIG. 4 illustrates the group changes in water intake. FIG. 4A shows that the normotensive group increased its intake during the captopril administration [$F(2,30)=16.3$, $p <0.01$] and that both doses were effective in this regard when compared to baseline levels of consumption ($T_{15}=4.2$, $p <0.01$-50 mg/kg; $T_{15}=5.0$, $p<0.01$-100 mg/kg). However, in the hypertensive group (FIG. 4B), water consumption was not significantly altered by the captopril administration [$F(2,20)=1.97$, n.s.].

Figure 5:
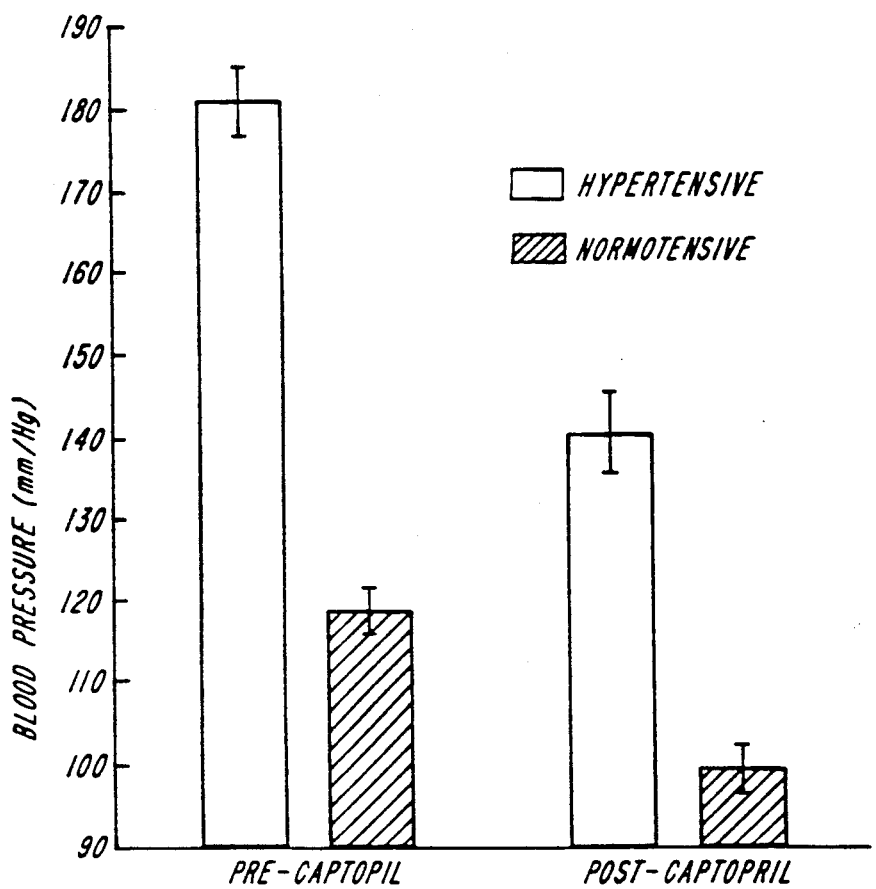
FIG. 5 is a bar diagram showing mean blood pressure in normotensive and hypertensive rats before and during captopril treatment. Vertical lines represent standard error of the mean.

FIG. 5 illustrates the mean blood pressure in both groups of animals of Example 2 before and after captopril administration. Captropril significantly lowered blood pressure in both the hypertensive ($T_{15}=4.57$, $p$ 0.01) and the normotensive groups ($T_{10}=5.2$, $p <0.01$).

The results of Example 2 confirm the findings of Example 1, in that captopril administration significantly attenuated voluntary alcohol drinking in normotensive animals Although there was a tendency for all doses to reduce intake in Example 1, only the 200 mg/kg dose significantly attenuated intake In Example 2, a significant reduction in alcohol intake was also achieved at a lower daily captopril dose (i.e., 100 mg/kg), suggesting that very high doses of captopril may be unnecessary to reduce alcohol intake While effective in the normotensive animals, captopril did not significantly reduce alcohol intake in the hypertensive group although there was a clear tendency in that direction. The increase in water intake in the normotensive group also replicates the findings of Example 1. The failure of the hypertensive group to show a similar increase in water intake may reflect a ceiling effect in that water intake was already enhanced as a consequence of the elevated plasma renin levels.

EXAMPLE 3

In Examples 1 and 2, doses of converting enzyme inhibitor were used which are known to elevate plasma renin activity (PRA) (Schiffrin et al., (1981). Proc. Soc. Exp. Biol. Med., v. 167, p. 327), and which reduced blood pressure (BP). These doses were large (i.e. 50 to 100 mg/kg b.i.d.) yet effective in reducing alcohol intake. Schiffrin et al. (Canadian J. Physiol. Pharmacol., (1984), v. 62, p. 116) have established that 1 mg/kg of Enalapril (Vasotec), another angiotensin converting enzyme inhibitor, does not elevate PRA or reduce BP in T-K,O-C hypertensive rats.

The third example shows the effect of this dose of enalapril on voluntary alcohol drinking. Because this is a rather low dose of the drug, it was important that alcohol intake occur in close temporal proximity to the administration of enalapril. We therefore used a limited access procedure which makes alcohol available for only 1 hr. per day. With this procedure most animals rapidly consume alcohol in quantities which produced detectable blood alcohol levels.

Subjects: The subjects were 32 naive male Wistar rats weighing 140 to 160 g. at the beginning of the study They were individually housed in cages equipped with water and food and kept on a reversed 12 hr/12 hr light/dark cycle with lights off at 7:00 a.m.

Procedure

Surgery: All animals underwent renal artery clipping as described in Example 2. Three weeks following the operation when both BP and PRA are known to be elevated, systolic BP was measured by the tail cuff method.

Alcohol drinking: The animals were divided into two groups, equated for BP, designated to be pretreated with either enalapril 1 mg/kg or saline vehicle. Every day, each animal was removed from its home cage and placed for 1 hr. in a "drinking" cage which had two graduated drinking tubes, one containing alcohol 3% (w/v) and the other water. The position of the two fluids was alternated daily and no food was available during this one hour period. After one hour had elapsed, the amounts of each fluid consumed were recorded and the animals returned to their home cages. One hour prior to placing the animals in the drinking cages, each animal received its respective i.p. injection of either enalapril (1 mg/kg) or saline.

At the conclusion of the study, BP was again measured in both groups.

Figure 6:
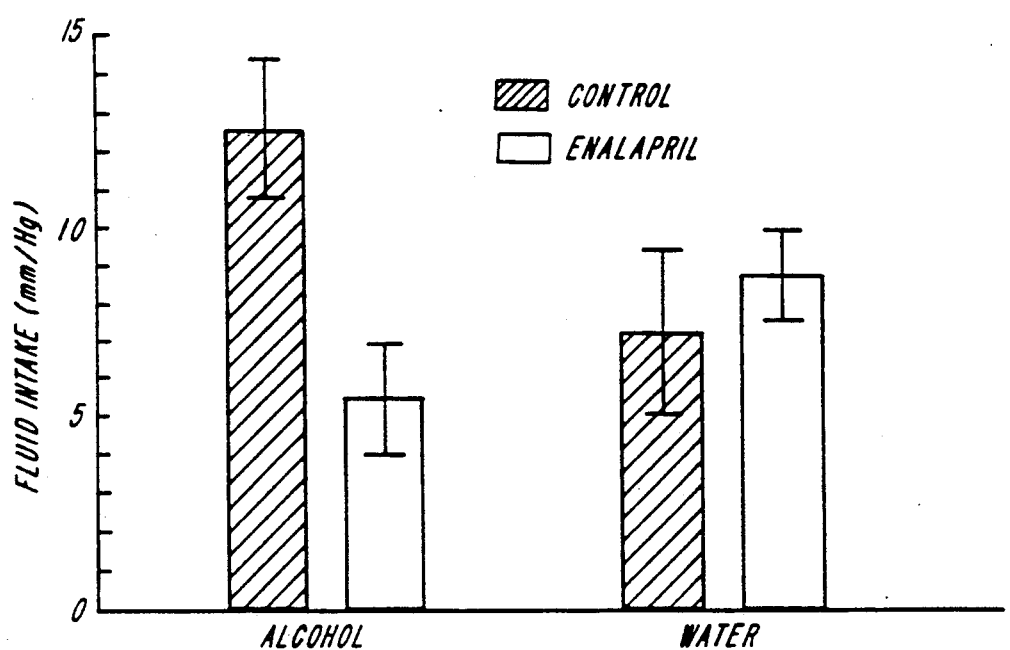
FIG. 6 is a bar diagram showing mean alcohol and water intake during a one hour period of access to alcohol. All animals were hypertensive; one group (open blocks) received i.p. injections of enalapril (1 mg/kg), the other group (shaded blocks) received injections of the vehicle (saline). Vertical lines represent the standard error of the mean.

FIG. 6 illustrates the alcohol intake for both groups averaged across the 14 days' study of Example 3 The T-K,O-C group pretreated with enalapril drank significantly less alcohol than the T-K,O-C group pretreated with the vehicle ($T_{30}=3.04$, $p <0.002$). Since 1 mg/kg enalapril has been found not to alter PRA, the present finding suggests that the ability of enalapril to reduce alcohol intake may not be dependent on a change in PRA.

Figure 7:
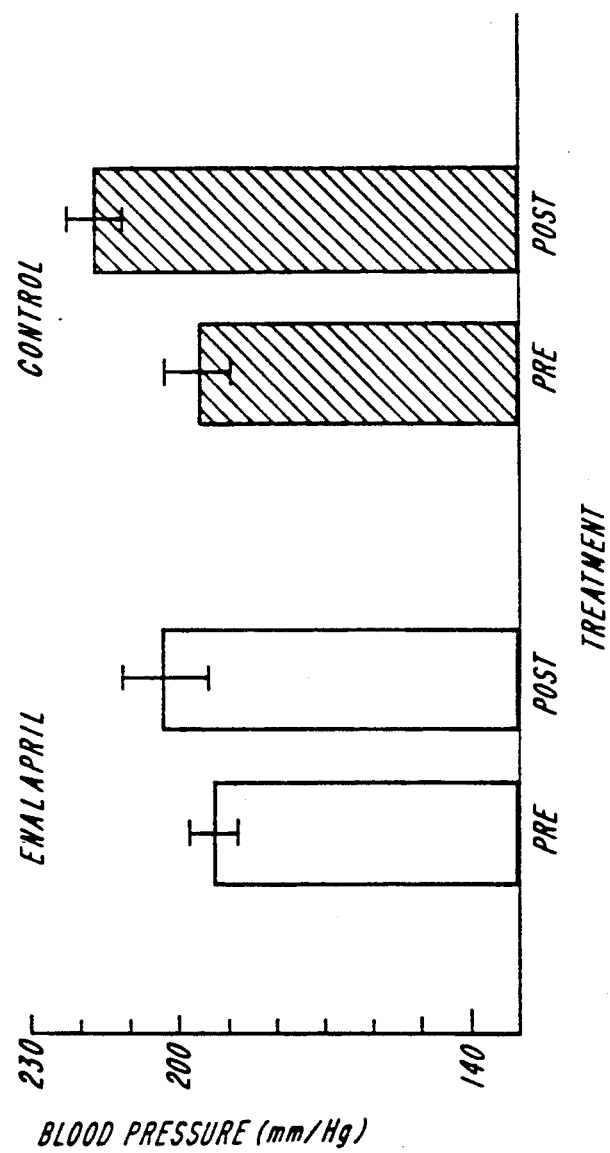
FIG. 7 is a bar diagram showing mean blood pressure in enalapril-treated and control (saline-treated) rats before and after drug treatment. All animals were rendered hypertensive by renal artery constriction. Vertical lines represent standard error of the mean.

FIG. 7 illustrates the average blood pressure for both groups of animals before and after pretreatment with enalapril or vehicle. As expected, the blood pressure of both groups was elevated following the T-K,O-C procedure (normal Wistar rat blood pressure 100–120 mm Hg.). Pretreatment with 1 mg/kg of enalapril daily for 14 days failed to reduce blood pressure ($T_{17}=1.02$, n.s) although blood pressure in the group receiving saline continued to rise ($T_{13}=3.08$, $p <0.5$). This finding is in agreement with Schiffrin et al. who also did not find a reduction in blood pressure in T-K,O-C rats even after twice daily treatment with 1 mg/kg of enalapril. These findings suggest that the ability of enalapril to reduce alcohol intake is not dependent upon a concurrent reduction in blood pressure.

FIG. 6 also shows the average water intake for both groups of rats in Example 3. Water intake was not significantly elevated in the T-K,O-C rats receiving enalapril. This confirms the suggestion that the 1 mg/kg dose of enalapril did not elevate PRA because the enhanced water intake sometimes associated with the administration of converting enzyme inhibitors is related to an elevated PRA. Furthermore, this finding demonstrates that the ability of enalapril to reduce alcohol intake does not depend on a concurrent change in the intake of water. This indicates that the 1 mg/kg dose of enalapril was specific in its ability to reduce voluntary alcohol drinking.

From the foregoing, it will be noted that ACE inhibitors, captopril and enalapril when administered to rats, produce a reduction of voluntary alcohol consumption.

It will also be noted that ACE inhibitors reduce voluntary alcohol consumption in rats whether alcohol is continuously available (when the animals typically drink in a number of short bouts distributed throughout the day) or is available only for one hour per day (when the animals typically drink in one or two extended bouts and consume in excess of their ability to metabolize alcohol).

Furthermore, in the case of the foregoing ACE inhibitors reduction of alcohol consumption was achieved in both normotensive and hypertensive animals. As shown by Example 2, captopril administration reduced blood pressure and alcohol consumption simultaneously. Since a significant number of alcoholics and heavy drinkers are hypertensive, the possibility arises of treating both conditions with the same medication.

EXAMPLE 4

This experiment documented the ability of the ACE inhibitor Abutapril (CGS-16617, Ciba-Geigy) to reduce voluntary alcohol intake and examined the effect of an opiate antagonist (Naltrexone) and an ANG II antagonist ([Sarl,Thr8]- ANG II) on the ACE inhibitor-mediated reduction in intake.

Subject: Twenty-five naive male Wistar rats (Charles River, Montreal) were used, weighing between 264-330 g at the beginning of the experiment. Rats were housed individually, had free access to food and water in their home cages, and were kept on a reverse 12-hour light-/dark cycle.

Procedure: Animals were offered alcohol using the limited access drinking procedure (24). Each day, during the dark cycle, animals were removed from their home cages, weighed, and then placed in individual drinking cages for 40 min. Two tubes, one containing a solution of alcohol, the other containing water were positioned on the front of each cage. No food was available during the alcohol access period. At the end of each 40 minute session the amounts of alcohol and water consumed were recorded and the animals returned to their home cages. The position of the two tubes was alternated daily to control for position preference. A stock solution of alcohol was prepared fresh weekly. For two weeks a 3% (w/v) alcohol solution was offered, followed by a 6% (w/v) solution for the remainder of the experiment. This procedure fosters voluntary alcohol intake in excess of the metabolic capacity of the animal (approximately 300 mg/kg/hr), yields detectable blood alcohol levels and produces pharmacologically relevant central nervous system effects (25). Data reported are based on the period when 6% alcohol was available.

Baseline: This phase consisted of 14 daily drinking sessions during which animals had access to 6% alcohol and water. At the end of this phase animals were divided into 4 groups matched for alcohol intake, and designated to receive either the saline vehicle (n=8), 5 mg/kg Abutapril (n=9), 10 mg/kg Abutapril (n=9) or 20 mg/kg Abutapril (n=9) in the following phase.

Abutapril Dose-Response: This phase consisted of two consecutive 7-day treatment periods (AB-week 1, AB-week 2) during which each group received its respective daily dose of Abutapril or saline vehicle by the intraperitoneal (i.p.) route one hour prior to alcohol access.

Abutapril-ANG II Antagonist: This phase, which followed the Abutapril Dose-Response phase, lasted 14 days during which only the Vehicle and 10 mg/kg Abutapril groups continued to be tested. Each group received two separate injections: first its respective daily dose of either Vehicle or Abutapril one hour prior to alcohol access and in addition, a subcutaneous (s.c.) saline injection during the first 5 and last 4 days of this phase, and a s.c. injection of the ANG II antagonist, (Sarl,Thr8)-ANG II (500 ug/kg), during the intermediate 5 days.

Abutapril-Opiate Antagonist: This final phase, which followed the Abutapril-ANG II antagonist phase, lasted 19 days during which both groups continued to receive their respective daily doses of either vehicle or Abutapril (10 mg/kg) one hour prior to alcohol access. Additionally, each group was administered saline for the first 4 and last 5 days of this phase and the opiate receptor antagonist (ORA), Naltrexone (2 mg/kg for the first 5 days; 10 mg/kg for the next 5 days), during the intermediate 10 days. Both vehicle and Naltrexone were given s.c. immediately prior to alcohol access.

Drugs: Abutapril (CGS-16617, Ciba-Geigy), the ANG II antagonist ([Sarl,Thr8]-ANG II, Sigma Chemical Co.) and the opiate antagonist (Naltrexone, Sigma Chemical Co.) Were dissolved in saline and prepared fresh daily just prior to their administration. The concentrations were adjusted so as to permit the administration of 0.1 ml/100 g body weight.

RESULTS

Effect of Abutapril on alcohol and water intake

Figure 8A:
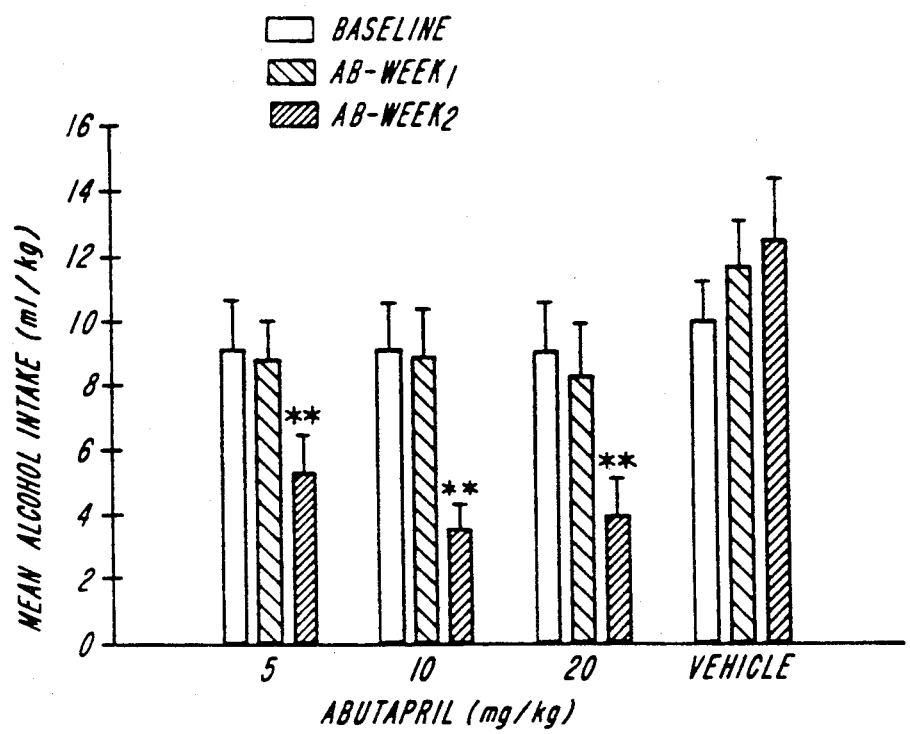
FIG. 8A is a bar diagram showing mean alcohol intake (ml/kg) in the saline vehicle group and the three Abutapril dose groups during baseline and two subsequent weeks of drug treatment AB-week one, AB-week two.

FIG. 8A shows the mean alcohol intake for the three Abutapril groups and the saline vehicle group during the Baseline and Dose-Response phases. Drinking for each animal was averaged across the 14 day Baseline and across each week of Abutapril treatment (AB-week 1, AB-week 2). A two-way analysis of variance with Dose as the between subjects factor and Phase and the within subjects factor yielded a significant effect of Phase $(F[2,48]=21.03, p<0.001)$ and a nonsignificant effect of Dose $(F[2,24]=0.09, NS)$ and Dose $\times$ Phase interaction $(F[2,24]=0.28, NS)$, indicating that Abutapril reduced alcohol intake to a similar degree at each dose tested. Post hoc tests showed that all three doses effectively reduced alcohol drinking, but only during the second week of treatment (5 mg/kg− T[8]=3.7, $p<0.01$; 10 mg/kg− T[8]=4,06, $p<0.01$; 20 mg/kg− T[8]=3.68, $p<0.01$). Saline treatment had no effect on alcohol consumption (AB-week 1 (T[7]=−1,126, NS); AB-week 2 (T[7]=−1.071, NS)).

Figure 8B:
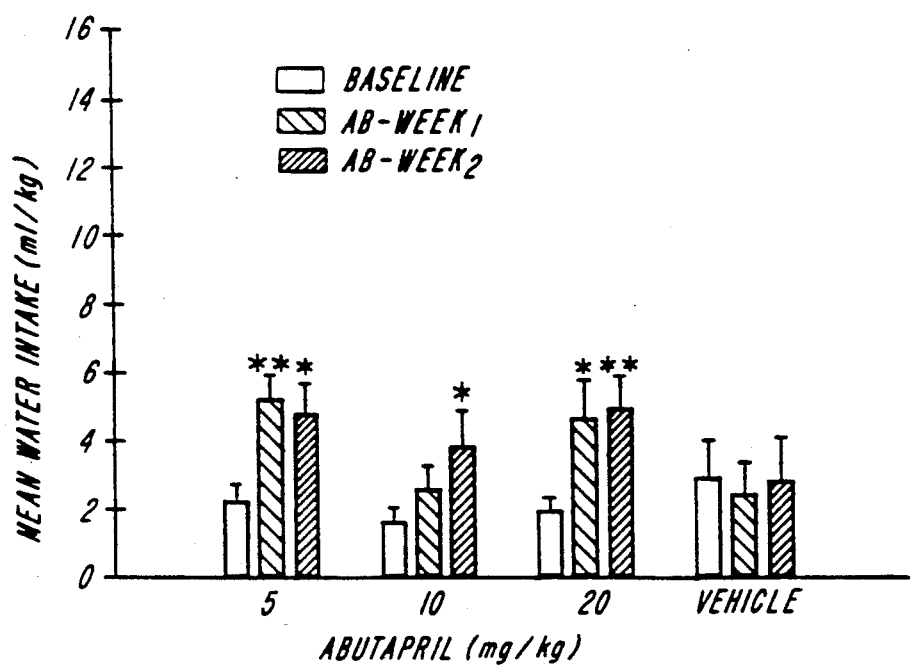
FIG. 8B is a bar diagram showing mean water intake (ml/kg) in the saline vehicle group and the three Abutapril dose groups during baseline and two subsequent weeks of drug treatment. Vertical lines represent the standard error of the mean. *$p < 0.05$; ** $p < 0.01$.

FIG. 8B illustrates the mean water intake for the Abutapril and saline vehicle treated groups across the Baseline and Dose-Response phases A two-way analysis of variance showed a significant effect of Phase ($F[2,48]=17.28$, $p<0.001$) indicating that Abutapril elevated water drinking, and a nonsignificant effect of Dose ($F[2,24]=1.27$, NS) and Dose×Phase interaction ($F[4,48]=1.07$, NS) showing that the doses used were equally effective in enhancing water intake Compared to Baseline, the groups receiving Abutapril 5 mg/kg ($T[8]=-4.14$, $p<0.01$) and 20 mg/kg ($T[8]=-3.19$, $p<0.05$), had significantly enhanced water intake during the first week. Water intake in the 10 mg/kg Abutapril group tended to increase, but did not reach statistical significance ($T[8]=-1.476$, NS). During the second week all three groups showed significantly elevated water consumption over Baseline Water intake in the saline treated animals remained unchanged during both week one ($T[7]=0.364$, NS) and week two ($T[7]=0.045$, NS).

Effect of (Sarl,Thr8)-ANG II on Abutapril-induced changes in alcohol and water intake.

Figure 9A:
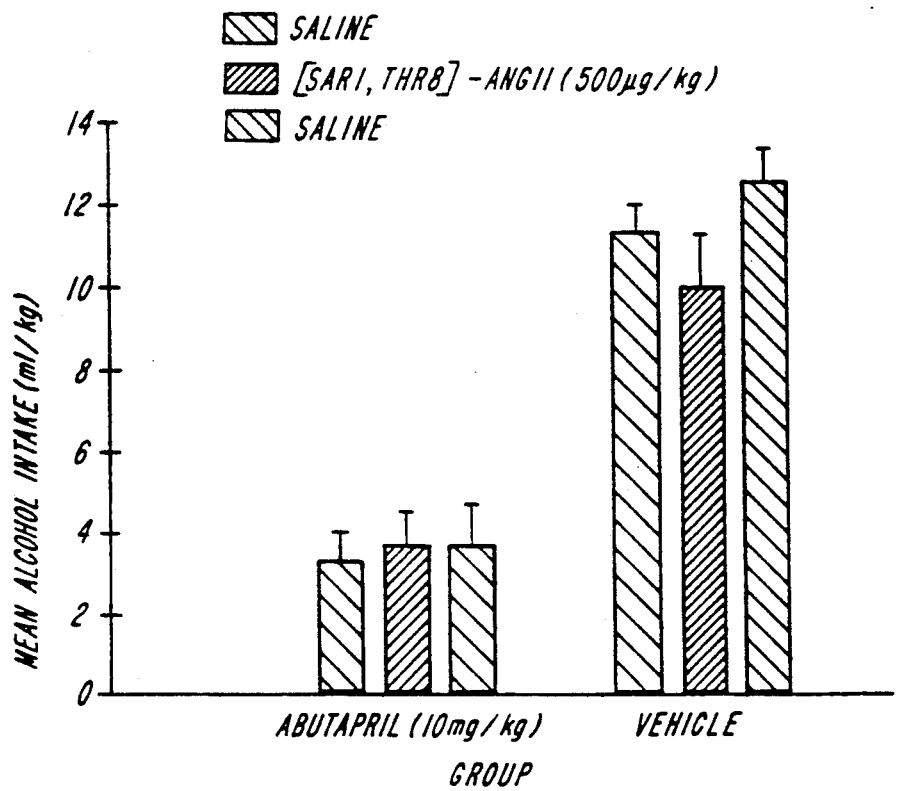
FIG. 9A is a bar diagram showing mean alcohol intake (ml/kg) in the saline vehicle group and the 10 mg/kg Abutapril treated group with (hatch block) and without (open block) the ANG II antagonist.

FIG. 9A profiles mean alcohol intake for the 10 mg/kg Abutapril and Vehicle groups over all three cycles of the Abutapril-ANG II antagonist phase. A two-way analysis of variance with Drug (Abutapril vs Vehicle) as the between subjects factor, and Cycle (Saline vs ANG II antagonist) as the within subjects factor yielded a significant effect of Drug ($F[1,15]=64.72$, $p<0.001$) indicating that Abutapril continued to decrease alcohol intake compared to Vehicle. A nonsignificant effect of Cycle ($F[2,30]=1.28$, NS) indicated that the ANG II antagonist was not able to reverse the effect of Abutapril on alcohol intake and a nonsignificant Drug×Cycle interaction ($F[2,30]=1.27$, NS) demonstrated that alcohol intake in the Abutapril and Vehicle groups did not change significantly across the three cycles of this phase. The latter finding replicated an earlier study validating the inability of (Sarl,Thr8)-ANG II by itself to produce any changes in alcohol consumption.

Figure 9B:
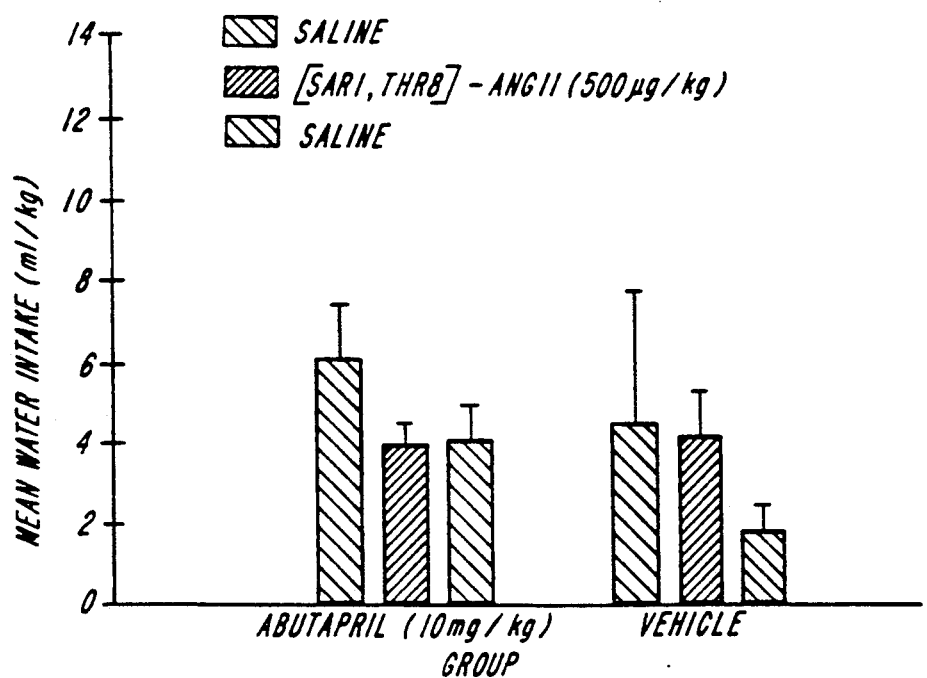
FIG. 9B is a bar diagram showing mean water intake (ml/kg) in the saline vehicle group and the 10 mg/kg Abutapril treated groups with (hatch block) and without (open block) the ANG ii antagonist.

FIG. 9B shows mean water intake for the 10 mg/kg Abutapril and Vehicle groups across the three cycles of this phase. The analysis revealed a nonsignificant effect of Drug ($F[1,15]=.58$, n.s.), Cycle ($F[2,30]=1.57$, n.s.) and Drug×Cycle interaction ($F[2,30]=0.47$, n.s.) demonstrating that water intake was similar for the Abutapril and Vehicle groups and was not markedly altered across the three cycles. This indicates that the antagonist alone, or in combination with Abutapril, did not modify water intake.

Effect of Naltrexone (ORA) on Abutapril-induced changes in alcohol and water intake.

Figure 10A:
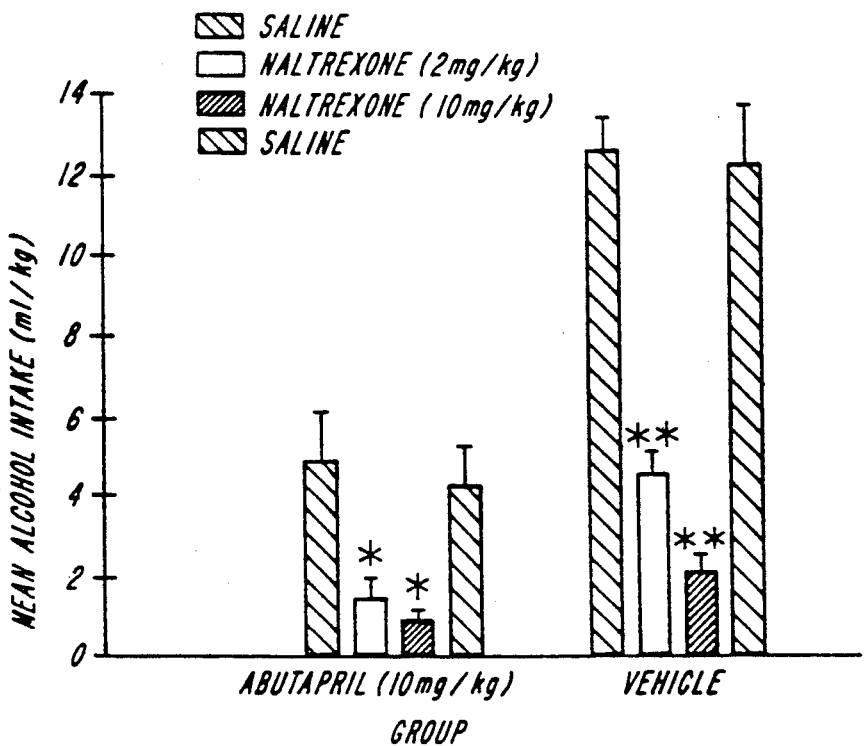
FIG. 10A is a bar diagram showing mean alcohol intake (ml/kg) in the saline vehicle group and the 10 mg/kg Abutapril treated groups with (Naltrexone 2, 10 mg/kg) and without (saline) Natrexone.

FIG. 10A illustrates the effect of (ORA) Naltrexone on alcohol intake in the Abutapril and Vehicle groups. Animals receiving (Sarl Thr8)-ANG II during the Abutapril-ANG II Antagonist phase were administered Naltrexone during this phase. A two-way analysis of variance yielded a significant effect of Drug ($F[1,15]=40.23$, $p<0.001$) indicating that Abutapril continued to suppress alcohol intake. A significant effect of Cycle ($F[3,45]=43.54$, $p<0.001$) and a significant Drug×Cycle interaction ($F[3,45]=9.23$, $p<0.001$) indicated that Naltrexone further reduced alcohol intake in both the Abutapril and Vehicle groups in a dose-dependent manner. Post hoc tests showed that both the 2 mg/kg ($T8=2.449$, $p<0.05$) and the 10 mg/kg ($T8=3.292$, $p<0.05$) doses of Naltrexone added to the suppression in intake already produced by Abutapril. Furthermore, Naltrexone by itself, produced a significant reduction in alcohol drinking in the Vehicle group (2 mg/kg ($T[7]=9.246$, $p<0.01$); 10 mg/kg ($T[7]=10.861$, $p<0.01$). Alcohol intake during the saline cycles did not change.

Figure 10B:
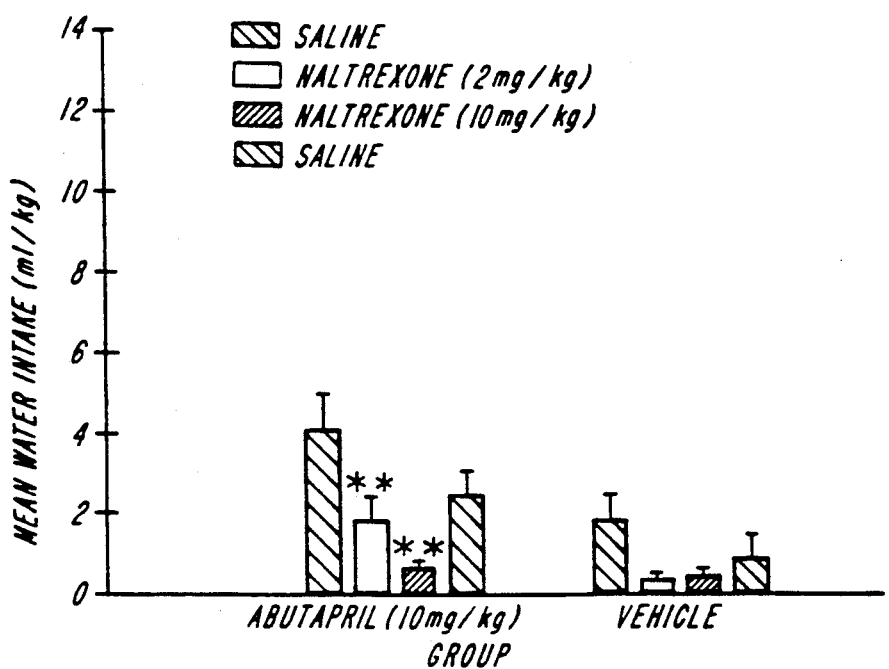
FIG. 10B is a bar diagram showing mean water intake (ml/kg) in the saline vehicle groups and the 10 mg/kg Abutapril treated groups with (Naltrexone 2, 10/ mg) and without (saline). Vertical lines represent the standard error of the mean. *p<0.05; ** p<0.01.

FIG. 10B demonstrated the effect of Naltrexone on water drinking in the Abutapril and Vehicle groups. The analysis of variance revealed a significant effect of Drug ($F[1,15]=5.191$, $p<0.02$) indicating that water intake was elevated in the Abutapril group compared to the Vehicle group. A significant effect of Cycle ($F[3,45]=9.08$, $p<0.001$), and a nonsignificant Drug×Cycle interaction ($F[3,45]=1.64$, NS) indicated that Naltrexone reduced water intake, but not in a dose-dependent manner. Post hoc tests determined that water intake in the Abutapril group was significantly suppressed by 2 mg/kg ($T[8]=-2.58$, $p<0.01$) and 10 mg/kg ($T[8]=3.9$, $p<0.01$) Naltrexone, but was unchanged in the Vehicle group (2 mg/kg ($T[7]=2.17$, NS); 10 mg/kg ($T[7]=1.977$, NS)). Water intake was not different during the saline cycle for either the Abutapril or Vehicle groups.

The present experiment shows that an ACE inhibitor can significantly reduce alcohol intake in normotensive Wistar rats. It also shows that the reduction in intake is not immediate but requires approximately one week to develop. The time course of the effect of Abutapril on alcohol intake is analogous to the blood pressure lowering effect of ACE inhibitors which is also more pronounced with time. In contrast to the effect on alcohol intake, the Abutapril-stimulated increase in water intake was present during the first week of treatment suggesting that mechanisms involved in enhanced water drinking are more sensitive to the ACE inhibitor than are those responsible for the reduction in alcohol intake. The time differential of the two effects also suggests that the reduction in alcohol intake is independent of and not simply a compensation for the increase in water intake.

The ANG II antagonist (Sarl,Thr8)-ANG II did not alter the ability of the ACE inhibitor to reduce the alcohol intake. Since this antagonist does not appear to enter the brain, its receptor blocking effects are limited to the periphery, specifically the circumventricular organs which are outside the blood-brain barrier. This indicates that ACE inhibitors are not acting through peripherally-based ANG II related processes to reduce alcohol consumption. Since peripheral administration of ACE inhibitors can elevate central RAS activity, the present findings indicate that if the reduction in alcohol intake produced by ACE inhibition is mediated through the RAS, the locus of this effect is likely to be at a central site not accessible to a peripherally administered ANG II antagonist.

Aside from their ability to block angiotensin converting enzyme, ACE inhibitors have also been shown to be enkephalinase inhibitors, the net result being an increase in the levels of endogenous enkephalin. The present study, however demonstrated that the opiate receptor antagonist, Naltrexone, could not alter the attenuation in alcohol intake produced by Abutapril, suggesting that ACE inhibitors do not produce their effects on alcohol intake by elevating enkephalin levels. Naltrexone is found to have an additive effect in that it further suppresses alcohol intake in the animals receiving Abutapril. This implies that the reduction in alcohol intake by the Naltrexone and that produce by the ACE inhibitor Abutapril might be mediated through two separate and different mechanisms.

EXAMPLE 5

Example 4 demonstrated that Abutapril can attentuate voluntary alcohol consumption in normotensive rats. Given the strong correlation between alcohol intake and hypertension in humans (e.g.19,20), together with the fact that alcoholics are frequently hypertensive and sometimes exhibit elevated RAS activity (e.g. 21), the following experiment assessed the effect of Abutapril on alcohol intake in hypertensive animals. The model of hypertension chosen was the Two-Kidney, One-Clip (2-K,1-C) hypertensive rat whose RAS is known to be elevated.

METHOD

Subject: The subjects were naive male Wistar rats weighing 138-179 g at the beginning of the experiment. They were individually housed, had free access to food and water and were kept on a reverse 12-hour light-/dark cycle.

Procedure: The animals were anaesthetized with a mixture of halothane, nitrous oxide and oxygen, and had a 0.2mm solid silver clip applied to the left renal artery. The right kidney was left untouched. After a 3 week recovery period systolic blood pressure was measured using the Lail-cuff method. Only those animals having blood pressure above 160 mmHg were offered limited access to alcohol as outlined in Example 3 (above). After a 14 day Baseline of alcohol 6% (w/v) and water access, animals were divided into two groups matched for alcohol intake an designated to receive either saline vehicle (n=9) or Abutapril 20 mg/kg (n=10). During the next 2 consecutive 7-day treatment periods (AB-week 1, AB-week 2), each group received its respective daily dose of Abutapril or saline vehicle by i.p. route one hour prior to alcohol access. Blood pressure was measured the 15th day, one hour after Abutapril treatment.

RESULTS

Figure 11A:
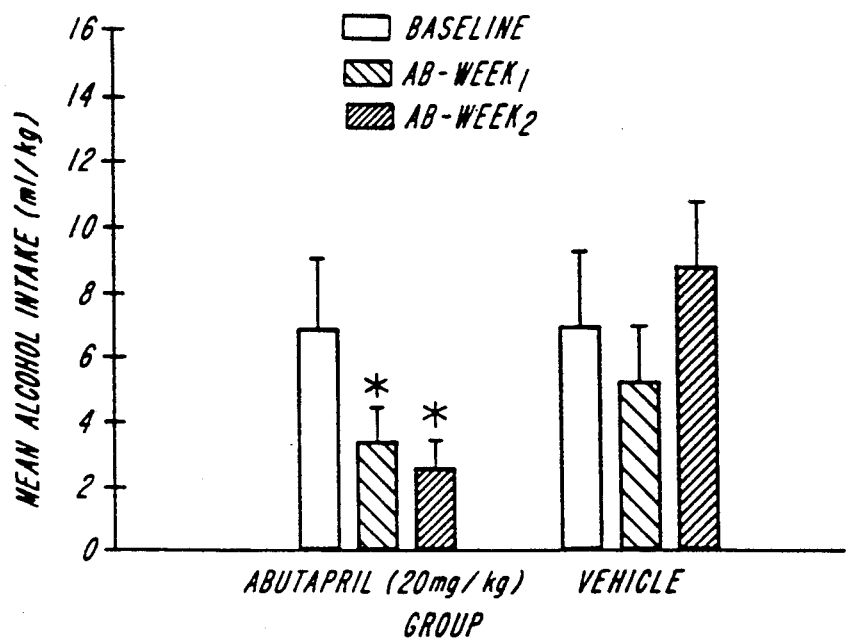
FIG. 11A is a bar diagram showing mean alcohol intake (ml/kg) in the 2K-1C renin-dependent hypertensive rats during baseline and the two week treatment period when each group received either the saline vehicle group or 20 mg/kg Abutapril.

FIG. 11A illustrates the effect of Abutapril on alcohol intake in the 2-K,-C (renin-dependent) hypertensive rats during the Baseline and Treatment periods. Alcohol intake was significantly reduced in the Abutapril group ($F[1,7]=5.357$, $p<0.03$), during both the first ($T[9]=2.2$, $p<0.05$), and the the Vehicle group did not change significantly during either week 1 ($T[8]=1.6$, NS) or week 2 ($T[8]=-0.877$, NS).

Figure 11B:
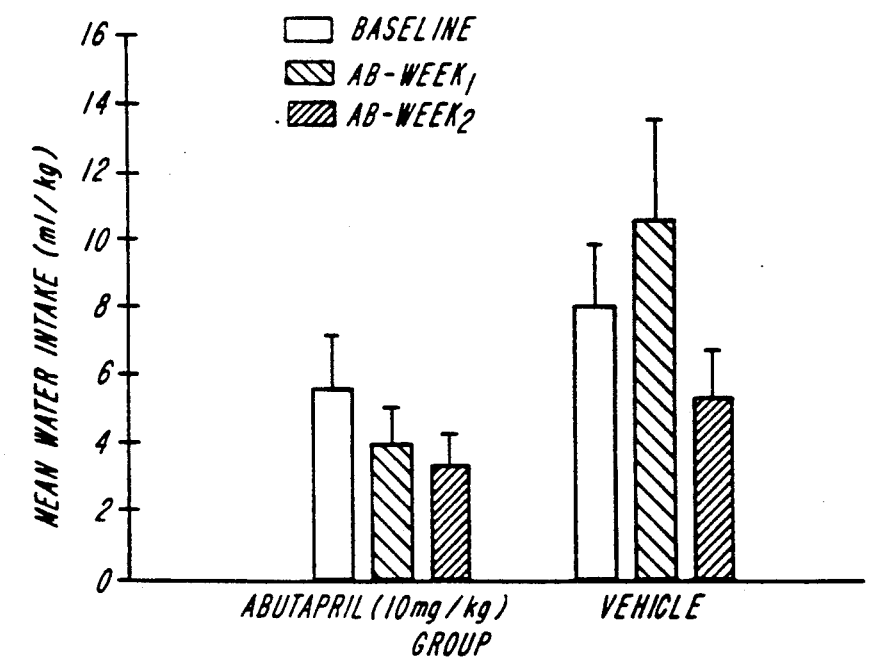
FIG. 11B is a bar diagram showing mean water intake (ml/kg) in the 2K-1C renin-dependent hypertensive rats during baseline and the two week treatment period when each group received either the saline vehicle group or 20 mg/kg Abutapril. Vertical lines represent the standard error of the mean. *p<0.05.

FIG. 11B illustrates the effect of Abutapril on water drinking in 2-K,1-C rats. Water intake across the Baseline and Treatment phases did not change for either the Abutapril or Vehicle groups ($F[2,34]=1.782$, NS). Although water intake in the Abutapril group is lower than that in the vehicle group ($F[1,17]=6.69$, $p<0.018$), reflects differential Baseline levels of water intake between the two groups rather than a particular effect of Abutapril.

Figure 12:
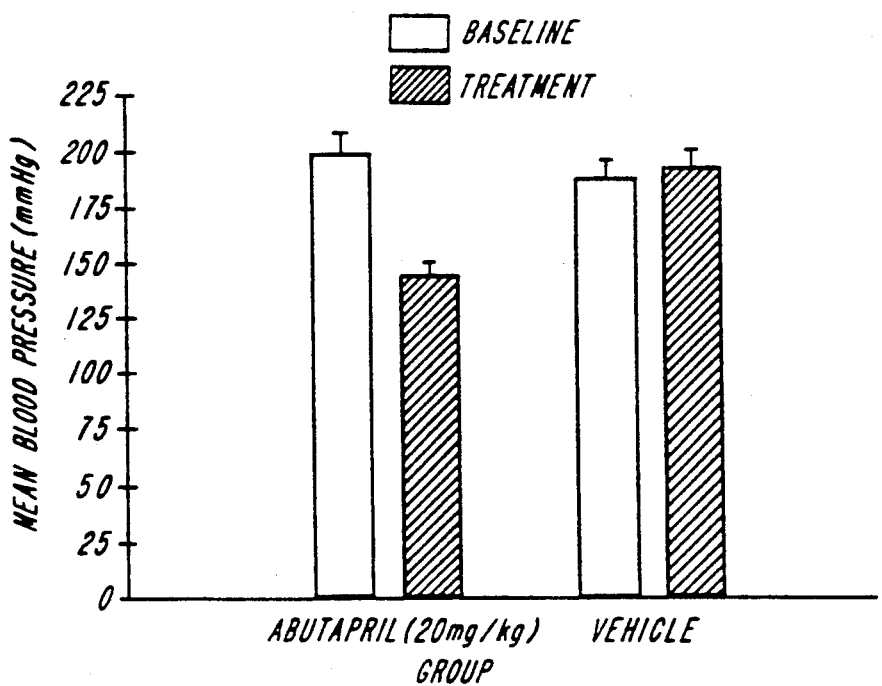
FIG. 12 is a bar diagram showing mean blood pressure (mmHg) in the 2-K,1-C hypertensive rats before (baseline) and after 14 days of Abutapril treatment. *p<0.05.

FIG. 12 illustrates mean blood pressure in both groups of 2-K,1-C animals before access to alcohol and after Abutapril or saline vehicle administration. Blood pressure was significantly lowered in the Abutapril-treated group ($T[8]=7.643$, $p<0.01$) while that of the saline group remained elevated ($T[7]=-0.737$, NS).

DISCUSSION

This Example 5 showed that the ACE inhibitor Abutapril can significantly reduce alcohol intake not only in normotensive rats but also in rats with elevated RAS activity i.e. the renin-dependent (2-K,1-C) hypertensive rats. This confirms earlier work with different ACE inhibitors. Whereas Abutapril (20 mg/kg) did not reduce alcohol intake in the normotensive animals of Example 4 until the second week of treatment, a robust reduction in the alcohol consumption of the 2-K,1-C rats was already apparent during the first week and continued strongly into the second week. This acceleration in the expression of the effect of Abutapril on alcohol intake comparing normotensive with 2-K,1-C hypertensive rats suggests that either basal levels of activity in the RAS or basal blood pressure levels may be variables in determining the course and perhaps also the strength of attenuation produced by ACE inhibitors. Earlier studies showed that elevated blood pressure is not always correlated with a suppressed alcohol intake. Taken together these findings show that alcohol intake of animals with elevated RAS activity is more sensitive to the suppressive effect of ACE inhibitors, and that initial levels of alcohol consumption, but are also relevant to the course of attenuation produced by the ACE inhibitors.

EXAMPLE 6

Example 5 suggests that the basal level of RAS activity is one variable which affects the responsiveness of ACE inhibitors to attenuate alcohol intake. In order to explore this relationship more fully the following experiment examined the effect of Abutapril on alcohol intake in a line of hypertensive rats (Dahl Salt-Sensitive [SS]) which have a suppressed level of activity in the RAS. If basal level is indeed an important variable then the Dahl (SS) rats should be less responsive to the attenuating effects of the ACE inhibitors on alcohol intake.

METHODS

Subjects: Thirty-five naive male Dahl SS weanling rats, approximately 8-9 weeks old were used. They were individually housed, had free access to food and water and were kept on a reverse 12-hour light/dark cycle.

Procedure: The weanling rats were fed a salt supplemented diet (8% NaCl) which consisted of standard powdered Purina rat chow with added powdered salt. As the animals became hypertensive over a 3 week period the salt concentration was reduced to 4% for 4 days and then back to the standard powdered Purina rat chow (0.4% NaCl) for the remainder of the experiment. Once hypertension has developed, it tends to be "self-sustaining" in that the hypertension remains even if the salt supplement is removed (36). After 6 days, blood pressure was measured using the tail-cuff method (34) and only those animals having blood pressure above 160 mmHg were used in the experiment Animals were then offered alcohol using the limited access procedure. After the first 7 days of 6% alcohol and water access (Baseline), animals underwent a 28 day Treatment phase where they were administered saline vehicle for the first and last 7 days, and Abutapril (20 mg/kg) during the intermediate 14 days. Such a design allowed each animal to act as it own control. Both saline vehicle and Abutapril were administered by i.p. injection one hour prior to alcohol access. Blood pressure was recorded once more on the fourteenth day of Abutapril treatment, one hour after Abutapril administration.

RESULTS

Figure 13A:
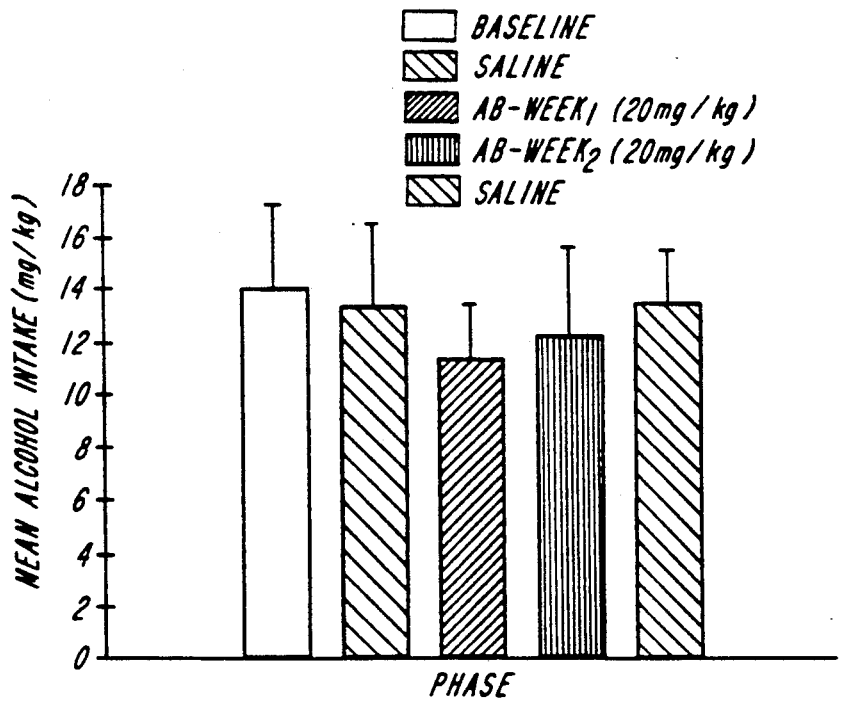
FIG. 13A is a bar diagram showing mean alcohol intake (ml/kg) in the low renin Dahl SS hypertensive rats during the five consecutive cycles of baseline, saline vehicle, the two week Abutapril treatment period and finally saline vehicle.

FIG. 13A shows the effect of Abutapril on alcohol drinking in Dahl SS hypertensive (low RAS) rats across the Baseline and Treatment phases. A one-way analysis of variance yielded a nonsignificant effect of phase ($F[7,28]=0.503$, NS) indicating that Abutapril failed to reduce alcohol consumption.

Figure 13B:
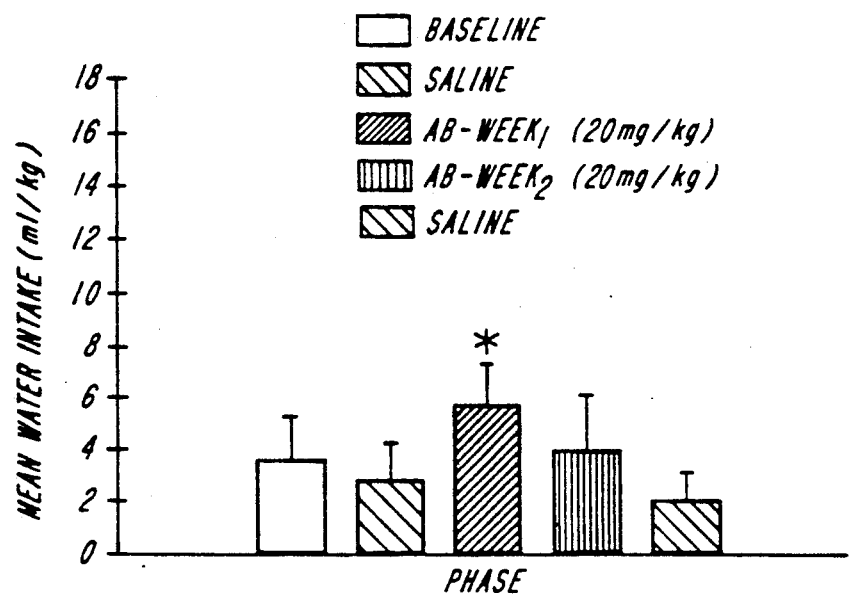
FIG. 13B is a bar diagram showing mean water intake (ml/kg) in the low renin Dahl SS hypertensive rats during the five consecutive cycles of baseline, saline vehicle the two week Abutapril treatment period and finally saline vehicle. Vertical lines represent the standard error of the mean. *p<0.05.

FIG. 13B illustrates changes in mean water intake across the Baseline and Treatment phases. A one-way analysis of variance showed that water intake was altered during the experiment ($F[7,28]=3.258$, $p<0.025$), and a post hoc test indicate water intake was significantly elevated during the first week of Abutarpil treatment ($T[7]=-2,927$, $p<0.05$).

Figure 14:
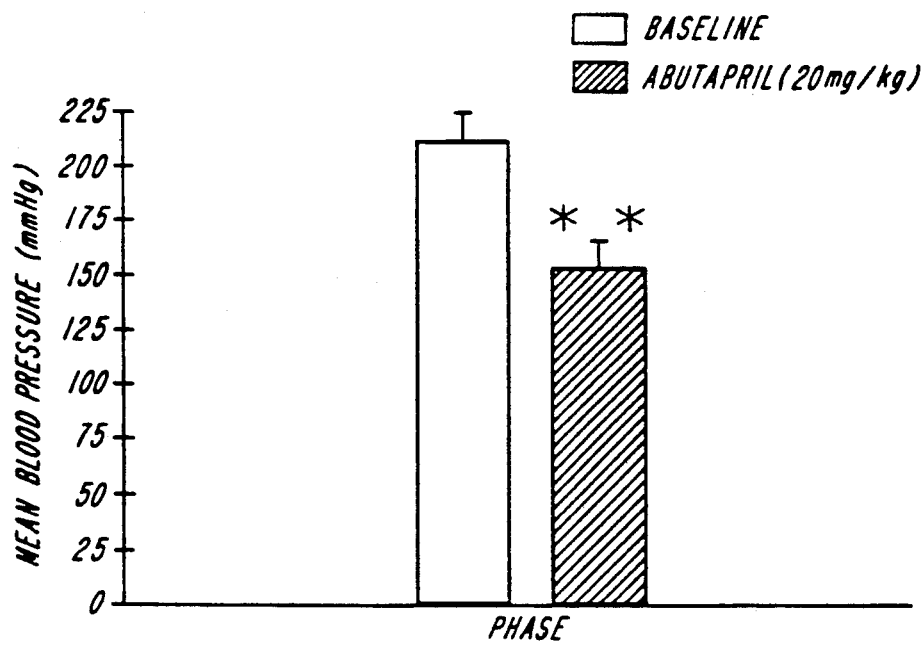
FIG. 14 is a bar diagram showing mean blood pressure (mmHg) in the Dahl SS hypertensive rats before (baseline) and during Abutapril treatment. Vertical lines represent the standard error of the mean. **p<0.01.

FIG. 14 gives the average blood pressure before and after Abutapril treatment. Abutapril significantly reduced blood pressure ($T[7]=7.596$, $p<0.01$).

DISCUSSION

This experiment shows that the ACE inhibitor Abutapril was unable to reduce alcohol intake in the Dahl SS line of hypertensive rats. Nevertheless water intake was increased and blood pressure significantly reduced suggesting that Abutapril was otherwise functional and capable of eliciting its other biological effects. The fact that the ACE inhibitor failed to reduce alcohol consumption in rats which are characterized by a suppressed RAS lends further support to the suggestion that the basal level of activity in the renin-angiotensin system (and not hypertension per se) plays an important role in determining the ability of ACE inhibitors to attenuate alcohol ingestion.

GENERAL DISCUSSION

The results of the present study confirm that a different ACE inhibitor-Abutapril (CGS 16617) produces a robust attenuation in alcohol intake. Given earlier evidence suggesting that opiates may regulate alcohol intake, together with the enkphalinase inhibiting properties of the ACE inhibitors, it is possible that the ACE inhibitor-induced reduction in alcohol intake is mediated through an increase in the endogenous enkephalins. However the administration of the opiate antagonist, Naltrexone, did not block the effect of Abutapril on alcohol intake, suggesting that these endogenous opiates are not involved in the reduction in alcohol drinking produced by Abutapril. Furthermore, since the effect of Naltrexone was additive to the effect of Abutapril, ACE inhibition and opiate receptor antagonism may be acting through different mechanisms to elicit similar effects on alcohol consumption.

The action of Abutapril on alcohol and water intake could not be reversed by administration of the ANG II receptor antagonist, (Sarl,Thr8)-ANG II. Furthermore, (Sarl,Thr8)-ANG II alone had no effect on alcohol and water drinking. Since this blocker does not penetrate the blood brain barrier, the effect of Abutapril on alcohol intake is not likely to be mediated via the peripheral renin-angiotensin system. This lends support to the notion (see below) that if ACE inhibitors attenuate alcohol intake through the RAS, the locus of this effect must be in the central nervous system itself.

The most important finding of these experiments is that the basal level of activity in the renin-angiotensin system is an important factor modulating the ability of the ACE inhibitors to reduce alcohol intake. Thus when RAS activity was either normal or elevated as in the case of normotensive or 2-K,1-C hypertensive rats, respectively, Abutapril produced a strong reduction in alcohol intake. Furthermore, the 2-K,1-C animals were more responsive to the ACE inhibitor-induced decrease in alcohol intake as shown by the earlier onset of effect. However in the case of the Dahl SS rats with suppressed RAS activity, Abutapril failed to have any impact on alcohol intake. Taken together these findings indicate that the effect of ACE inhibitors on alcohol intake is dependent on the status of the RAS at the time of administration.

How do the ACE inhibitors reduce alcohol intake? While nothing definitive is known, several interesting and testable possibilities do present themselves. First, ACE inhibitors produce an increase in plasma renin activity and ANG I because a decrease in ANG II synthesis removes the feedback inhibition on renin release. Although ANG I cannot be converted to ANG II in the periphery because of the presence of the ACE inhibitor, it can be converted to the naturally occurring ANG I fragment (Des Asp-1) ANG I because ACE inhibitors cannot inhibit the aminopeptidases. If this fragment of ANG I is active and can reduce alcohol intake, it may mediate some of the effects of Abutapril on alcohol intake.

A second possibility makes reference to a "spill-over" hypothesis which attempts to explain the paradoxical thirst and sodium appetite produced by the ACE inhibitors. According to this hypothesis, the elevated concentrations of ANG I in the plasma which occur during treatment With ACE inhibitors gain access to brain site not accessible to the ACE inhibitors themselves. There, ANG I is coverted to ANG II and hence produces a response - in the present case a reduction in alcohol intake. Experimental support for this suggestion has come from work showing that the potentiating effect on water intake by a peripherally administered ACE inhibitor could be blocked by concomitant central ACE inhibition (29,40). It is therefore possible that as a consequence of lowering peripheral ANG II, the ACE inhibitors may also produce a site-specific elevation in central ANG II levels which mediate the reduction in alcohol consumption.

If elevated (central) peptide levels are an important part of the effect of Abutapril and other ACE inhibitors on alcohol intake, it has been suggested that the process involved may be a satiety mechanism. This mechanism would monitor levels of activity in the RAS and send a "stop" signal to shut off alcohol intake once RAS activity enters some critical or "satiety" range. Thus any manipulation which would alter basal levels of RAS activity would have the potential to increase intake if the basal level were to be shifted away from the satiety range or to decrease intake if basal levels were elevated closer to the putative satiety range. In the context of the present experiments, the failure of the Dahl SS rats to respond to ACE inhibitor treatment would be related to the low level of basal RAS activity. On the other hand, the ability of Abutapril to reduce alcohol intake in the normotensive rats and the increased responsiveness in the 2-K,1-C rats would be related to their normal and elevated levels of basal RAS activity respectively.

In summary, these experiments have shown that a normal or elevated RAS system is an important setting condition for at least certain of the ACE inhibitors to function. Their ability to reduce alcohol intake in human subjects remains to be assessed, but pretreatment screening of RAS activity levels may be useful in studying this drug clinically and in selecting those patients who are most likely to benefit.

EXAMPLE 7

The two-kidney one-clip (T-K,O-C) model of hypertension is one in which plasma renin activity is elevated, and is also referred to as renin-dependent hypertension. Previous experiments have shown that T-K,O-C rats consume less alcohol than sham-operated controls, perhaps because of the elevated r-a activity they exhibit. The present experiment assessed the ability of ACE inhibitors, Abutapril, Benzapril and Enalapril to reduce alcohol intake in animals with elevated r-a activity.

METHOD

Subject: Thirty-seven experimentally naive male Wistar rats (Charles River, Montreal) were used, weighing 138-178 g at the beginning of the experiment. The animals were individually housed, had free access to food and water and were kept on a reversed 12-hour light/dark cycle with lights off at 7:00 am. This experiment was performed in two separate replications and individual means for alcohol intake in each were derived across the 14 day Baseline phase and across the two weeks of the Treatment phase (designated $week_1$ and $week_2$). A two-way analysis of variance was used to compare the saline groups of each replication, with group as the between subjects factor, and phase as the within subjects factor. Because the analysis yielded a nonsignificant effect of group [$F(1,7)=0.222$, NS] and phase [$F(1,7)=0.064$, NS]; and a nonsignificant group×phase interaction [$F(1,7)=0.302$, NS], the data from the two replications was combined. Each experimental grou had either nine or ten subjects.

Surgery: The animals were anaesthetized with a mixture of halothane, nitrous oxide and oxygen, and had a 0.2 mm solid silver slip applied to the left renal artery. The right kidney was left untouched. After a three week recovery period systolic blood pressure was measured using the tail cuff procedure (Section 1.7.2). Only those animals having blood pressure above 160 mmHg were used.

Procedure

Baseline: This phase consisted of 14 daily drinking trials, at the end of which animals were assigned to four groups having equal mean alcohol consumption.

Treatment: This phase consisted of two consecutive 7 day periods (designated $week_1$ and $week_2$) during which each group received its designated daily dose of either saline (n=9) or 20 mg/kg of Abutapril (n=10), Benzapril (n=9) or Enalapril (n=9) by intraperitoneal injection one hour prior to alcohol access. Blood pressure was measured using the tail-cuff procedure (Section 1.7.2.) before the Baseline phase and on the fifteenth day of the Treatment phase to assess the ability of each ACE inhibitor to reduce blood pressure. Each group received its respective ACE inhibitor treatment one hour before blood pressure monitoring.

Results

FIG. 15A summarizes the mean alcohol consumption for the saline control and the three ACE inhibitor treated T-K,O-C groups, during the Baseline and Treatment phases. The drinking for each animal was averaged across the fourteen day Baseline phase and across each week of ACE inhibitor treatment. A two-way analysis of variance with drug as the between subjects factor and phase as the within subjects factor was carried out. The analyses revealed a significant effect of phase [$F(2,50)=6.50$, $p<0.003$] indicating that ACE inhibition did attenuate alcohol intake; a nonsignificant effect of drug [$F(2,25)=.04$, NS] and a nonsignificant drug×phase interaction [$F(4,50)=0.16$, NS] showing that in those phases where alcohol intake was decreased, the reduction was similar for each ACE inhibitor. Post hoc tests revealed that compared to Baseline, alcohol intake was significantly decreased during both Week 1 and week 2 of the Treatment phases for all ACE inhibitors. Alcohol intake in the saline control group was unchanged. These data show that alcohol drinking was suppressed by Abutapril and Enalapril as found in Examples 4 and 5. However, Benzapril which had no affect on alcohol ingestion in normotensive animals was able to decrease alcohol intake in renin-dependent hypertensive rats. In addition, all three inhibitors lowered alcohol drinking during the first week of ACE inhibition while in the normotensive rats of Example 5, the effect on alcohol was not found until the second week. Taken together these findings suggest that converting enzyme inhibition exerts a more profound effect in hypertensive rats with elevated r-a activity than in normotensive rats with unaltered r-a activity.

Mean water consumption data is illustrated in FIG. 16B. A two-way analysis of variance showed a significant effect of drug [$F(2,25)=4.06$, $p<0.02$] which reflects the different initial (Baseline) levels of water drinking, and does not appear to be a particular effect of any one ACE inhibitor. The analyses also Yielded a nonsignificant drug×phase interaction [$F(2,50)=0.49$, NS] and a nonsignificant drug×phase interaction [$F(4,50)=0.73$, NS] indicating that none of the ACE inhibitors altered water intake across the Baseline and Treatment phases. These findings demonstrate that while alcohol intake is reduced in T-K,O-C rats, water drinking appears to be unaffected by converting enzyme inhibition. The stimulated r-a activity produced by the T-K,O-C manipulation enhances basal water intake and most likely does not allow for further elevations in water drinking following ACE inhibition.

FIG. 16C illustrates the blood pressure in the T-K,O-C rats before and after administration of the ACE inhibitors. Since blood pressure in Wistar rats normally ranges between 100-120 mmHg it is clear that all four T-K,O-C groups were hypertensive. A two-way analysis of variance with drug as the between subjects factor, and phase as the within subjects factor revealed a significant effect of phase [$F(1,25)=51.92$, $p<0.001$] indicating that ACE inhibition attenuated blood pressure. A nonsignificant effect of drug [$F(2,25)=.90$] and a nonsignificant drug×phase interaction [$F(2,25)=2.38$, NS] revealed that the reduction produced was similar for each ACE inhibitor. Post hoc analyses indicated that blood pressure was significantly reduced by Abutapril ($T_9=7.643$, $p<0.01$); Benzapril ($T_8=2.791$, $p<0.05$); and Enalapril ($T_8=3.639$, $p<0.01$). Blood pressure readings in the saline treated group were not significantly altered ($T_7=-0.737$, NS).

DISCUSSION

This sixth experiment showed the 20 mg/kg Abutapril, Benzapril and Enalapril all significantly attentuated alcohol consumption, and that the reduction was apparent during both the first and second weeks of treatment. This contrasts with the results from the previous experiment where Abutapril (20 mg/kg) decreased alcohol drinking in normotensive animals only during the second week of treatment. The results also show that Benzapril which did not elicit a response in normotensive animals was able to produce a significant decrease in alcohol intake in T-K,O-C animals. Taken together these finding suggest that the initial level of activity in the renin-angiotensin system may be an important factor in determining the degree of attenuation of alcohol intake produced by ACE inhibition.

This experiment has shown that ACE inhibition did not alter voluntary alcohol drinking in low renin Dahl salt-sensitive hypertensive rats. The 20 mg/kg dose of Abutapril, proven effective in its ability to reduce alcohol intake in normotensive and high renin T-K,O-C hypertensive rats, was unable to reduce alcohol intake in Dahl SS low renin rats. Although alcohol drinking was not suppressed by ACE inhibition, water intake was elevated. This finding again reflects the greater sensitivity of water intake to the effect of converting enzyme inhibition. Blood pressure, which was increased as a result of the salt supplemented diet, was lowered by Abutapril administration. These changes in water intake and blood pressure levels suggests that while Abutapril effectively inhibited angiotensin converting enzyme, the stimulation of re activity was not great enough to alter alcohol intake.

In summary, we have confirmed the ability of ACE inhibition to specifically modulate alcohol and water intake in different directions has been confirmed. ACE inhibition does reduce alcohol intake, and certain ACE inhibitors are more effective than others in eliciting this response when PRA levels are in the normal range. Furthermore, it appears that neither peripheral ANG II receptors, nor the endogenous opiate system mediate lowered alcohol consumption via ACE inhibition. It has been shown that ACE inhibition can decrease alcohol consumption in both normotensive and hypertensive animals and that hypertension is not a prerequisite for this response as revealed by the lack of alcohol reduction in Dahl SS rats. Most importantly we have found that the ability of ACE inhibition to attenuate alcohol consumption may be a function of pretreatment RAS activity, where the greater the level of activity, the more effective ACE inhibition will be in attenuating alcohol consumption.

Other ACE inhibitors such as ZOFENOPRIL, ALACEPRIL, RENTIAPRIL, DUINAPRIL, SPIRAPRIL, CILAZAPRIL, FOSINOPRIL, DELAPRIL, PERINDOPRIL, and RANAPRIL as alternatives will have similar characteristics and may be conveniently employed.

From the foregoing, it will be seen that an effective method of treatment without harmful side-effects has been provided whereby the voluntary alcohol consumption of warm blooded animals is reduced under a wide variety of conditions.

What we claim by Letters Patent of the United States, is:

1. A method of treating warm-blooded animals in need thereof so as to reduce their voluntary alcohol consumption which comprises administering a therapeutically effective amount of an angiotensin converting enzyme inhibitor to said animals.

2. A method according to claim 1 wherein the angiotensin converting enzyme inhibitor is selected from the group consisting of abutapril and benzapril.

3. A method of treating warm-blooded animals so as to reduce their voluntary alcohol consumption which comprises administering to an animal in need thereof an angiotensin converting enzyme inhibitor in a therapeutically effective dose.

4. A method of reducing voluntary alcohol consumption in warm-blooded animals in need thereof which comprises administering to said animals an angiotensin converting enzyme inhibitor in a dose in the range of 1 to 100 mg/kg body weight/day.

5. A method for treatment of alcoholism, comprising administering to a warm-blooded animal in need thereof a therapeutically effective amount of an angiotensin converting enzyme inhibitor selected from the group consisting of abutapril and benzapril.

6. A method for treatment of alcoholism, comprising administering to a warm-blooded animal in need thereof a therapeutically effective amount of a therapeutic composition comprising an angiotensin converting enzyme inhibitor selected from the group consisting of abutapril and benzapril, and a pharamaceutically acceptable carrier.

7. A method of reducing voluntary alcohol consumption in warm-blooded animals in need thereof which comprises administering to said animals an angiotensin converting enzyme inhibitor in a dose in the range of 1 to 200 mg/kg body weight/day, and an opiate receptor antagonist in a dose in the range of 2 to 10 mg/kg body weight/day.

8. A method of treating a warm-blooded animal in need thereof to reduce voluntary alcohol consumption comprising administering to said animal an angiotensin converting enzyme inhibitor wherein the inhibitor contains a seven-membered hetero ring containing one or two nitrogen atoms, and selected from the group consisting of abutapril, benzapril, cilazapril and CGS-14832, said inhibitor being administered in a therapeutically effective amount.

9. A method of treating warm-blooded animals so as to reduce their voluntary alcohol consumption as set forth in claim 8 which comprises administering abutapril in a dose of at least approximately 5 mg/kg body weight/day.

10. The method of treating warm-blooded animals so as to reduce their voluntary alcohol consumption as set forth in claim 8, which comprises administering benzapril in a dose of at least approximately 20 mg/kg body weight/day.

11. A method of treating warm blooded animals in need of treatment to reduce their voluntary alcohol consumption which comprises administering to said animals a therapeutically effective amount of an angiotensin converting enzyme inhibitor selected from the group consisting of abutapril and benzapril.

* * * * *

UNITED STATES PATENT AND TRADEMARK OFFICE
CERTIFICATE OF CORRECTION

PATENT NO. : 5,110,813
DATED : May 5, 1992
INVENTOR(S) : Larry A. Grupp, et al.

It is certified that error appears in the above—identified patent and that said Letters Patent is hereby corrected as shown below:

Column 7, line 44, "p 0.01" should read --p<0.01--.

Column 9, line 44, "=4.57, p" should read --=4.57, p<--.

Column 15, line 51, after "," insert --and the second weeks of Treatment (T[9]=2.5, p<0.05).--.

Column 19, line 36, "grou" should read --group--.

Column 15, line 51, "And the the" should read --Alcohol intake in the--.

Signed and Sealed this

Twenty-fifth Day of January, 1994

Attest:

BRUCE LEHMAN

Attesting Officer     Commissioner of Patents and Trademarks